United States Patent
Gross et al.

(10) Patent No.: US 8,864,849 B1
(45) Date of Patent: *Oct. 21, 2014

(54) ANIONIC AZO DYESTUFFS FOR COLORING KERATIN-CONTAINING FIBERS

(71) Applicant: Henkel AG & Co. KGaA, Düsseldorf (DE)

(72) Inventors: Wibke Gross, Hückelhoven (DE); Ralph Nemitz, Jüchen (DE); Melanie Moch, Dormagen (DE); Astrid Kroos, Monheim (DE); Antje Gebert, Düsseldorfer (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/271,211

(22) Filed: May 6, 2014

Related U.S. Application Data

(63) Continuation of application No. PCT/EP2012/071814, filed on Nov. 5, 2012.

(30) Foreign Application Priority Data

Nov. 8, 2011 (DE) .......................... 10 2011 085 907
Feb. 24, 2012 (DE) .......................... 10 2012 202 818

(51) Int. Cl.
  *A61Q 5/10* (2006.01)
  *C07D 277/42* (2006.01)
  *C07D 211/00* (2006.01)
  *A61K 8/46* (2006.01)

(52) U.S. Cl.
  CPC .. *A61K 8/463* (2013.01); *A61Q 5/10* (2013.01)
  USPC ................ 8/405; 8/409; 8/568; 8/570; 8/573; 548/146; 548/215; 548/300.1; 548/355.1; 546/249

(58) Field of Classification Search
  USPC .............. 8/405, 409, 568, 570, 573; 548/146, 548/215, 300.1, 355.1; 546/249
  See application file for complete search history.

(56) References Cited

FOREIGN PATENT DOCUMENTS

| DE | 2317133 | 10/1974 | |
|----|---------|---------|---|
| EP | 1915984 A1 * | 10/2006 | ............... A61Q 5/10 |
| EP | 1915984 A1 | 4/2008 | |

OTHER PUBLICATIONS

STIC Search Report dated May 30, 2014.*
Shibusawa. Takao et al: "Dyeing properties of disperse dyes. VI. Interactions between .beta.-cyclodextrin and 4-aminoazobenzene derivatives and the effect of the interactions on the dyeing properties of 4-aminoazobenzene derivatives" Nippon Kagaku Kaishi ( 12). 2171-7 Coden: NKAKB8; ISSN: 0369-4577, Sep. 1975, XP9166395, pp. 2173-2177.

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

The present specification provides for an agent for coloring keratinic fibers. The agent includes, a cosmetic carrier, a compound of formula (I),

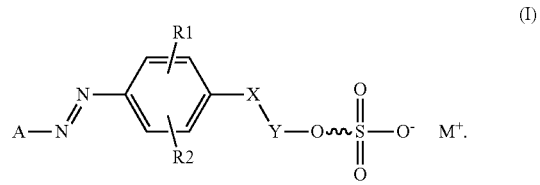

(I)

R1 and R2 independently of one another denote hydrogen, a $C_1$-$C_6$ alkyl group, a $C_2$-$C_6$ alkenyl group, a hydroxyl group, a halogen, a $C_1$-$C_6$ alkoxy group, an amino group, a nitro group, an acetyl amino group, or a sulfonamide group; or when in ortho-position to one another, form a 5- or 6-membered, saturated or unsaturated ring, which optionally include further heteroatoms.

15 Claims, No Drawings

ANIONIC AZO DYESTUFFS FOR COLORING KERATIN-CONTAINING FIBERS

FIELD OF THE INVENTION

The present application generally relates to an agent for coloring keratinic fibers. More particularly, the present application relates to azo dyes in agents for coloring and optionally simultaneously lightening keratin-containing fibers, in particular human hair.

BACKGROUND OF THE INVENTION

In general substantive dyes or oxidation dyes are used for coloring keratinic fibers. Although intense colors with good fastness properties can be obtained with oxidation dyes, the development of the color generally takes place under the influence of oxidizing agents such as, for example, $H_2O_2$, which in some cases may result in damage to the fiber. Furthermore, some oxidation dye precursors, or certain mixtures of oxidation dye precursors, may have a sensitizing effect on people with sensitive skin. Substantive dyes are applied under gentler conditions. The disadvantage of these dyes, however, lies in the fact that the colors often have inadequate fastness properties, in particular with regard to hair washing, but also in respect of external influences, such as sunlight, or reactive environmental chemicals, such as swimming pool water. Substantive dyes are also used for shading oxidative colors.

Achieving a uniform coloring of frequently pretreated hair, such as bleached or permanently waved hair where the fibers have very differing degrees of pre-damage in the various lengths or variously treated areas, represents a particular challenge in terms of coloring hair with substantive dyes. For example, during the coloring process itself, a coloring agent can produce an uneven coloring on differently pre-damaged hair, while repeated hair washing can also cause the dyes to be washed out of the different areas of the hair to varying degrees, resulting in an inconsistent and hence undesirable color result.

In another example, for extreme lightening of dark hair, not only hydrogen peroxide alone but a combination of hydrogen peroxide and persulfates (e.g. ammonium persulfate, potassium persulfate and/or sodium persulfate) is used. Thus, if dark hair is to be significantly lightened in a single step and colored in a bright shade at the same time, the use of a mixture of hydrogen peroxide, persulfates and a substantive dye is advantageous. Although many intensely coloring substantive dyes are used, a very limited choice of dyes is available that can withstand the strong oxidative conditions created by mixing the aforementioned oxidizing agents without breaking down. In addition, the oxidation-stable dyes may have serious disadvantages in terms of their other fastness properties.

Therefore, for the simultaneous coloring and extreme lightening of hair there is a need for dyes having high stability with respect to strong oxidizing agents. Even under these extreme application conditions, these dyes should not lose their positive fastness and coloring properties.

Accordingly, an object of the present specification is to provide coloring agents for keratinic fibers, in particular human hair, having novel substantive dyes, which in terms of color depth and fastness properties (in particular light fastness, rubbing fastness, wash fastness, perspiration fastness, and cold wave fastness), have good application properties. It is also particularly desirable to provide coloring agents having a good equalizing capacity. In cases where they are used at the same time as oxidation dyes and/or oxidizing agents, the substantive dyes may have adequate stability in respect of hydrogen peroxide and other oxidizing agents and may not lose their positive fastness and coloring properties. In addition, the colors obtained should be as bright and intense as possible.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

The present specification describes an agent for coloring keratinic fibers, in particular human hair. The agent includes, in a cosmetic carrier, at least one compound of formula (I),

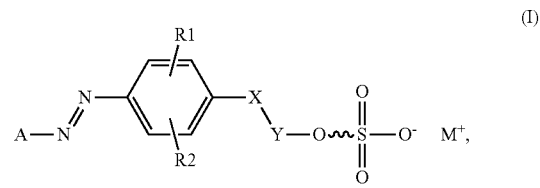

in which R1 and R2 independently of one another denote hydrogen, a $C_1$-$C_6$ alkyl group, a $C_2$-$C_6$ alkenyl group, a hydroxyl group, a halogen, a $C_1$-$C_6$ alkoxy group, an amino group, a nitro group, an acetyl amino group or a sulfonamide group, or when R1 and R2 are in ortho-position to one another, form a 5- or 6-membered, saturated or unsaturated ring, which can optionally include further heteroatoms. Also, X denotes O or N—R3, R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a cyano-$C_1$-$C_6$ alkyl group or a —Y'—O—$SO_2$—O$^-$ M$^+$ group, Y and Y' independently of one another denote $(CH_2)_n$ or $C_2H_4$—$(OC_2H_4)_n$ or $(CH_2)_n$—O—$(CH_2)_m$ or $(CH_2)_n$—N(R6')-$(CH_2)_m$ and n and optionally m each denote a whole number from 1 to 6. Also A denotes one of the structures (II) to (XV),

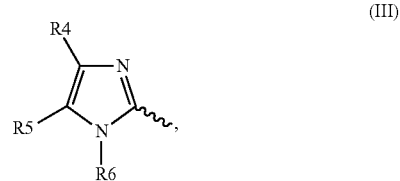

-continued

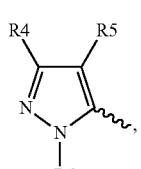
(V)

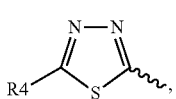
(VI)

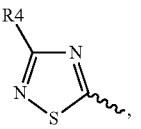
(VII)

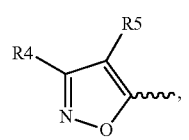
(VIII)

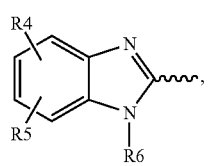
(IX)

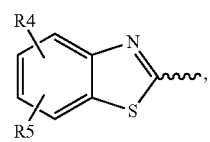
(X)

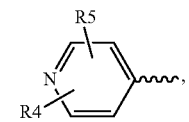
(XI)

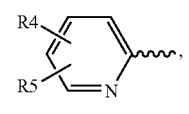
(XII)

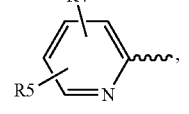
(XIII)

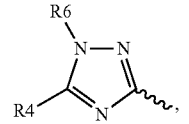
(XIV)

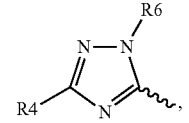
(XV)

R4 and R5 independently of one another denote hydrogen, an amino group, a $C_1$-$C_6$ alkylamino group, a di-($C_1$-$C_6$ alkyl) amino group, a hydroxyl group, a $C_1$-$C_6$ alkoxy group, a $C_1$-$C_6$ alkyl group, a $C_2$-$C_6$ alkenyl group, a carboxylic acid group, a sulfonic acid group, halogen, an acetylamino group or a sulfonamide group, or R4 and R5, when in ortho-position to one another, form a 5- or 6-membered, saturated or unsaturated ring, which can optionally include further heteroatoms, R6 and R6' independently of one another denote a hydrogen atom, a $C_1$-$C_6$ alkyl group, a $C_2$-$C_6$ alkenyl group or a $C_2$-$C_6$ hydroxyalkyl group, and $M^+$ denotes a proton ($H^+$), an alkali metal cation or a half equivalent of an alkaline-earth metal cation.

The present specification describes one compound of formula (I),

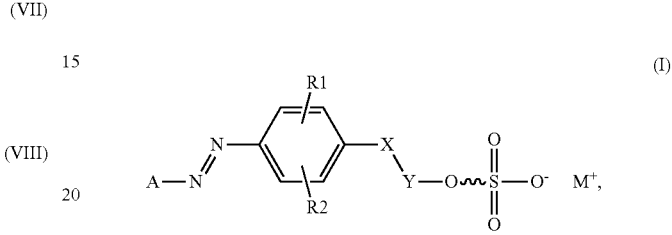
(I)

in which R1 and R2 independently of one another denote hydrogen, a $C_1$-$C_6$ alkyl group, a $C_2$-$C_6$ alkenyl group, a hydroxyl group, a halogen, a $C_1$-$C_6$ alkoxy group, an amino group, a nitro group, an acetyl amino group or a sulfonamide group, or when R1 and R2 are in ortho-position to one another, form a 5- or 6-membered, saturated or unsaturated ring, which can optionally include further heteroatoms. Also, X denotes O or N—R3, R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a cyano-$C_1$-$C_6$ alkyl group or a —Y'—O—$SO_2$—$O^-$ $M^+$ group, Y and Y' independently of one another denote $(CH_2)_n$ or $C_2H_4$—$(OC_2H_4)_n$ or $(CH_2)_n$—O—$(CH_2)_m$ or $(CH_2)_n$—N(R6')-$(CH_2)_m$ and n and optionally m each denote a whole number from 1 to 6. Also A denotes one of the structures (II) to (XV),

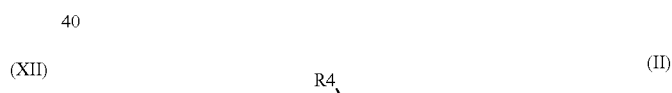
(II)

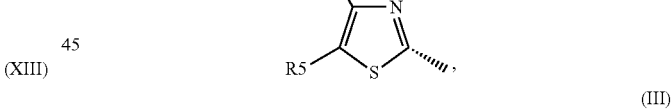
(III)

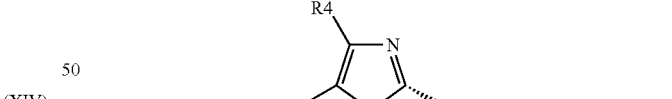
(IV)

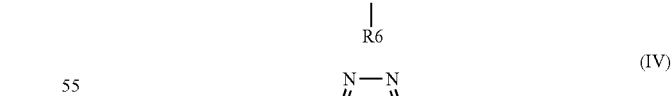
(V)

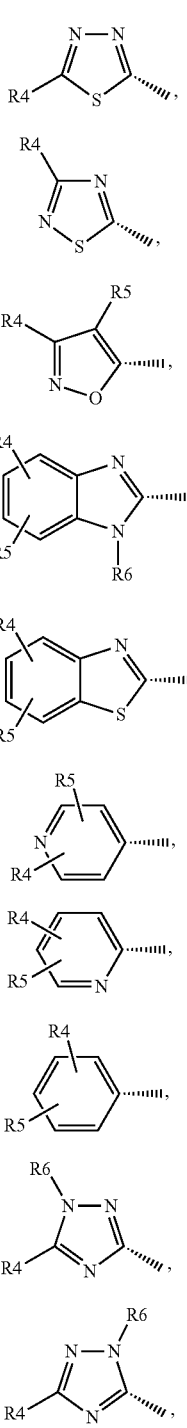

R4 and R5 independently of one another denote hydrogen, an amino group, a $C_1$-$C_6$ alkylamino group, a di-($C_1$-$C_6$ alkyl) amino group, a hydroxyl group, a $C_1$-$C_6$ alkoxy group, a $C_1$-$C_6$ alkyl group, a $C_2$-$C_6$ alkenyl group, a carboxylic acid group, a sulfonic acid group, halogen, an acetylamino group or a sulfonamide group, or R4 and R5, when in ortho-position to one another, form a 5- or 6-membered, saturated or unsaturated ring, which can optionally include further heteroatoms, R6 and R6' independently of one another denote a hydrogen atom, a $C_1$-$C_6$ alkyl group, a $C_2$-$C_6$ alkenyl group or a $C_2$-$C_6$ hydroxyalkyl group, and $M^+$ denotes a proton ($H^+$), an alkali metal cation or a half equivalent of an alkaline-earth metal cation.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Certain anionic azo dyes having a sulfate unit bound to the azo chromophore by means of a linker unit are very suitable as substantive dyes for hair coloring. In a pigment removal process, intense color shades can be obtained with very good fastness properties, in particular also in the presence of oxidizing agents.

These substantive dyes likewise deliver intense shades with no weakening of color intensity and color brilliance when used at the same time as oxidizing agents such as hydrogen peroxide or a mixture of hydrogen peroxide and peroxo disulfates (persulfates). In this way hair can be simultaneously lightened and colored, allowing a bright color to be achieved even on dark hair.

Azo dyes including a cationic, specifically substituted thiazole unit may be used as hair coloring agents, as described in EP 1915984. These dye molecules include a phenylazo unit, which can be alkyl-substituted with a sulfuric acid function. However, these dyes are not suitable for producing particularly bright colors.

Accordingly, coloring agents including compounds of the azo dye type according to formula (I) below have hitherto been unknown as hair dyes.

As used in the present specification and in the appended claims, the term "keratinic fibers," "keratin-containing fibers," "keratin fibers" or similar terms refer to fur, wool, feathers and in particular human hair. Although the agents according to the present specification are primarily suitable for lightening keratin fibers, there is nothing in principle to preclude their use in other fields.

As used in the present specification and in the appended claims, the term "coloring of keratin fibers" includes any form of color changing of fibers. It includes in particular the color changes covered by the terms "toning," "bleaching," "oxidative coloring," "semi-permanent coloring," "permanent coloring," and "temporary coloring." It also includes color changes according to the present specification characterized by a lighter color result in comparison to the original color, such as for example a coloring bleaching process.

The agents according to the present specification include the compounds of formula (I) in a cosmetic carrier. This cosmetic carrier is preferably aqueous, alcoholic, or aqueous-alcoholic. For the purposes of hair treatment, such carriers may be for example creams, emulsions, gels, or surfactant-containing foaming solutions, such as for example shampoos, foam aerosols, or other preparations that are suitable for use on the hair. In some examples, the formulation is provided as a powder or a tablet for storage purposes. Before use, it is mixed with an aqueous solvent, with organic solvents, or with mixtures of water and organic solvents to obtain an application mixture. An aqueous carrier includes, within the meaning of the present specification, at least 40 wt. %, in particular at least 50 wt. %, of water. Within the meaning of the present specification, "aqueous-alcoholic carriers" refer to hydrous compositions including 3 to 70 wt. % of a $C_1$ to $C_4$ alcohol, in particular ethanol or isopropanol. The agents according to the present specification may additionally include further organic solvents, such as for example 4-methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred here. Preferred agents according to the present specification are characterized in that they additionally include a non-aqueous solvent, wherein preferred agents according to the present specification include the solvent in a concentration from 0.1 to 30 wt. %, preferably in a concentration from 1 to 20 wt. %, and most particularly preferably in a concentration from 2 to 10 wt. %, relative in each case to the agent.

Examples of the substituents R1, R2, R3, R4, R5, R6 and R6' specified in formula (I) are given below by way of example. Examples of $C_1$ to $C_6$ alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. Particularly preferred alkyl residues are methyl and ethyl. Examples of $C_2$-$C_6$ alkenyl groups are vinyl, prop-2-enyl (allyl), 2-methyl prop-2-enyl, but-3-enyl, but-2-enyl, pent-4-enyl or pent-3-enyl. Examples of $C_2$-$C_6$ hydroxyalkyl groups are —$CH_2CH_2OH$, —$CH_2CH_2CH_2OH$, —$CH_2CH(OH)CH_3$, —$CH_2CH_2CH_2CH_2OH$, the —$CH_2CH_2OH$ group being preferred. Examples of $C_2$-$C_6$ polyhydroxyalkyl groups are 1,2-dihydroxyethyl, 2,3-dihydroxypropyl, 3,4-dihydroxybutyl and 2,4-dihydroxybutyl. Examples of $C_1$-$C_6$ alkoxy groups are methoxy and ethoxy, preferably methoxy. Examples of cyano-$C_1$-$C_6$ alkyl groups are cyanomethyl and 2-cyanoethyl. Examples of halogen are fluorine, chlorine, bromine or iodine, in particular fluorine and chlorine. Examples of $C_1$-$C_6$ alkoxy groups are methoxy or ethoxy. Examples of $C_1$-$C_6$ alkylamino groups are methylamino, ethylamino and propylamino. Examples of di($C_1$-$C_6$ alkyl) amino groups are dimethylamino, diethylamino and dipropylamino.

Preferred residues A are thiazole groups (II), imidazole groups (III), triazole groups (IV)/(XIV), thiadiazole groups (VI)/(VII), and benzothiazole groups (X).

According to the present specification, the agent is characterized in that it includes a compound of formula (I), in which A denotes one of the structures (II), (III), (IV), (VI), (VII), (X) or (XIV), in particular (II), (IV) or (X).

In a preferred example, A denotes a 1,3-thiazol-2-yl group (II), preferably a 1,3-thiazol-2-yl group in which R4 and R5 each denote hydrogen.

In another preferred example, A denotes an imidazol-2-yl group (III), preferably an imidazol-2-yl group in which R4, R5 and R6 each denote hydrogen.

In another preferred example, A denotes a 4H-1,2,4-triazol-3-yl group (IV), preferably a 4H-1,2,4-triazol-3-yl group in which R4 and R6 each denote hydrogen.

In another preferred example, A denotes a 4H-1,2,4-triazol-3-yl group (IV), preferably a 4H-1,2,4-triazol-3-yl group in which R4 denotes hydrogen and R6 denotes methyl.

In another preferred example, A denotes a 1H-1,2,4-triazol-3-yl group (XIV), preferably a 1H-1,2,4-triazol-3-yl group in which R4 and R6 each denote hydrogen.

In another preferred example, denotes a 1H-1,2,4-triazol-3-yl group (XIV), preferably a 1H-1,2,4-triazol-3-yl group in which R4 denotes hydrogen and R6 denotes methyl.

In another preferred example, denotes a 1,3,4-thiadiazol-2-yl group (VI), preferably a 1,3,4-thiadiazol-2-yl group in which R4 denotes hydrogen.

In another preferred example, denotes a 1,2,4-thiadiazol-5-yl group (VII), preferably a 1,2,4-thiadiazol-5-yl group in which R4 denotes hydrogen.

Very good results are obtained when the sulfate unit is bound by an amino group to the phenylazo unit, preferably an aminoalkyl unit.

In another example of the present specification, the agent includes a compound according to formula (I) and X denotes N—R3 and Y denotes $(CH_2)_n$, where n equals 2 or 3.

When X denotes N—R3, the agents according to the present specification may include doubly uncharged compounds as the compound of formula (I), where R3 denotes a —Y'—O—$SO_2$—$O^-$ $M^+$ group. However, compounds of formula (I) that are preferred according to the present specification includes one anionic grouping. Preferably, X denotes N—R3 and R3 denotes a $C_1$-$C_6$ alkyl group. In another example of the present specification, an agent includes a compound of formula (I) in which X denotes N—R3 and R3 denotes a $C_1$-$C_6$ alkyl group, in particular methyl or ethyl.

In a preferred example, the agent according to the present specification includes at least one compound of formula (I) and A denotes a 1,3-thiazol-2-yl group (II) in which R4 and R5 each denote hydrogen, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I) and A denotes a 1,3-thiazol-2-yl group (II) in which R4 and R5 each denote hydrogen, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I) and A denotes an imidazol-2-yl group (III) in which R4, R5 and R6 each denote hydrogen, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I) and A denotes an imidazol-2-yl group (III) in which R4, R5 and R6 each denote hydrogen, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I) and A denotes a 4H-1,2,4-triazol-3-yl group (IV) in which R4 and R6 each denote hydrogen, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I) and A denotes a 4H-1,2,4-triazol-3-yl group (IV), R4 and R6 each denote hydrogen, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I) and A denotes a 4H-1,2,4-triazol-3-yl group (IV), R4 denotes hydrogen and R6 denotes methyl, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I), A denotes a 4H-1,2,4-triazol-3-yl group (IV), R4 denotes hydrogen and R6 denotes methyl, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I), A denotes a 1H-1,2,4-triazol-3-yl group (XIV), R4 and R6 each denote hydrogen, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I), A denotes a 1H-1,2,4-triazol-3-yl group (XIV), R4 and R6 each denote hydrogen, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I), A denotes a 1H-1,2,4-triazol-3-yl group (XIV), R4 denotes hydrogen and R6 denotes methyl, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I), A denotes a 1H-1,2,4-triazol-3-yl group (XIV), R4 denotes hydrogen and R6 denotes methyl, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I), A denotes a 1,3,4-thiadiazol-2-yl group (VI), R4 denotes hydrogen, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I), A denotes a 1,3,4-thiadiazol-2-yl group (VI), R4 denotes hydrogen, X denotes N—R3, Y denotes $(CH_2)_n$ where n equals 3, and R3 denotes a $C_1$-$C_6$ alkyl group, preferably methyl or ethyl.

In another preferred example, the agent according to the present specification includes at least one compound of formula (I), A denotes a 1,2,4-thiadiazol-5-yl group (VI), R4 denotes hydrogen, X denotes N—R3, Y denotes $(CH_2)_n$ where n equals 2, and R3 denotes a $C_1$-$C_6$ alkyl group, preferably methyl or ethyl.

In another preferred example, the agent according to the present specification includes at least one compound of formula (I), A denotes a 1,2,4-thiadiazol-5-yl group (VI), R4 denotes hydrogen, X denotes N—R3, Y denotes $(CH_2)_n$ where n equals 3, and R3 denotes a $C_1$-$C_6$ alkyl group, preferably methyl or ethyl.

Furthermore, the residues R1 and R2 independently of one another preferably denote a hydrogen atom, a $C_1$-$C_6$ alkyl group, a halogen atom, or a $C_1$-$C_6$ alkoxy group. It is particularly preferable if R1 and R2 independently of one another denote a hydrogen atom, a $C_1$-$C_6$ alkyl group, or a nitro group. In particular, both R1 and R2 denote a hydrogen atom or one of the residues R1 and R2 denotes hydrogen and the other denotes a nitro group.

In another preferred example, the agent according to the present specification includes at least one compound of formula (I) and R1 and R2 independently of one another denote hydrogen, a $C_1$-$C_6$ alkyl group, or a nitro group, R1 and R2 preferably each denoting hydrogen or R1 preferably denoting hydrogen and R2 a nitro group.

In a further preferred example, the residues R4 and R5 independently of one another denote a hydrogen atom, a $C_1$-$C_6$ alkyl group, a $C_1$-$C_6$ alkoxy group, a halogen atom, a $C_1$-$C_6$ alkylsulfonyl group, or a nitrile group.

In a further preferred example, the residues R6 and/or R6' each independently of one another denote a hydrogen atom or a $C_1$-$C_6$ alkyl group, in particular a hydrogen atom or a methyl group.

According to the present specification, M is a group that neutralizes the anionic sulfuric acid ester grouping. Compounds in which M is a proton ($H^+$) or an alkali metal cation, in particular sodium or potassium ($Na^+$, $K^+$), meet the stated object of the present specification to a special degree and are therefore preferred.

Agents for coloring and optionally simultaneously lightening keratinic fibers that are preferred according to the present specification are characterized in that they include at least one compound of the general formula (I) selected from the following group:

2-{methyl[4-(1,3-thiazol-2-yldiazenyl)phenyl]amino}ethyl hydrogen sulfate,

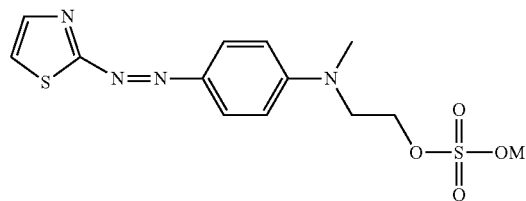

$M = H^+, Na^+, K^+$

2-{ethyl[4-(1,3-thiazol-2-yldiazenyl)phenyl]amino}ethyl hydrogen sulfate,

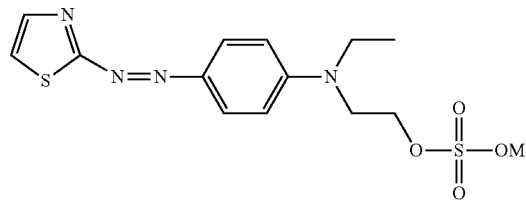

$M = H^+, Na^+, K^+$

3-{methyl[4-(1,3-thiazol-2-yldiazenyl)phenyl] amino}propyl hydrogen sulfate,

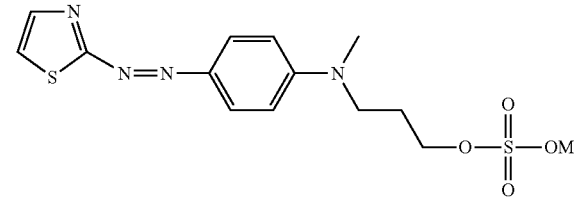

$M = H^+, Na^+, K^+$

3-{ethyl[4-(1,3-thiazol-2-yldiazenyl)phenyl]amino}propyl hydrogen sulfate,

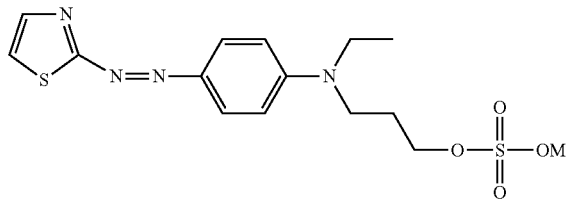

M = H⁺, Na⁺, K⁺

2-{methyl[3-methyl-4-(1,3-thiazol-2-yldiazenyl)phenyl]amino}ethyl hydrogen sulfate,

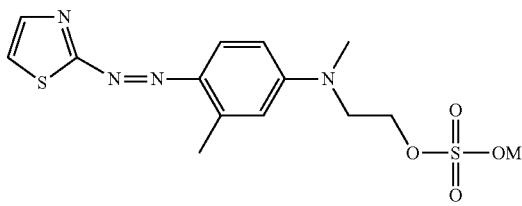

M = H⁺, Na⁺, K⁺

3-{ethyl[3-methyl-4-(1,3-thiazol-2-yldiazenyl)phenyl]amino}propyl hydrogen sulfate,

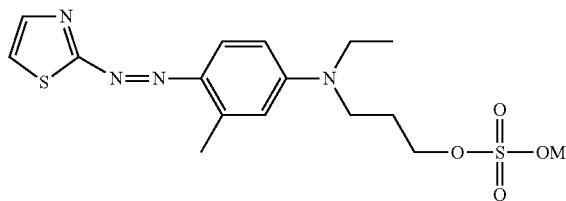

M = H⁺, Na⁺, K⁺

2-{[4-(1H-imidazol-2-yldiazenyl)phenyl](methyl)amino}ethyl hydrogen sulfate,

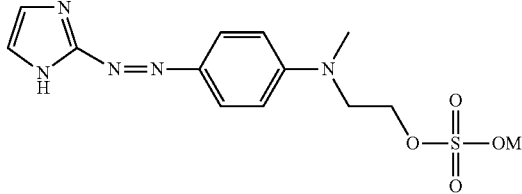

M = H⁺, Na⁺, K⁺

2-{ethyl[4-(1H-imidazol-2-yldiazenyl)phenyl]amino}ethyl hydrogen sulfate,

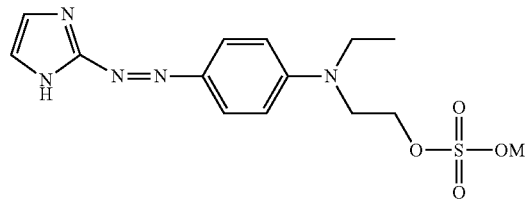

M = H⁺, Na⁺, K⁺

3-{ethyl[4-(1H-imidazol-2-yldiazenyl)phenyl]amino}propyl hydrogen sulfate,

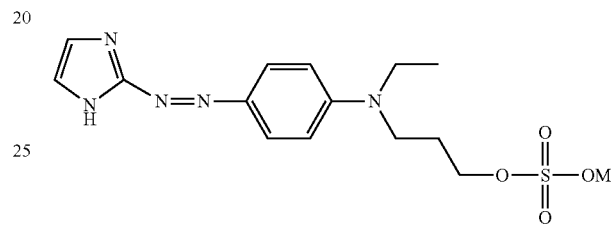

M = H⁺, Na⁺, K⁺

2-{ethyl[4-(1H-imidazol-2-yldiazenyl)-3-methylphenyl]amino}ethyl hydrogen sulfate,

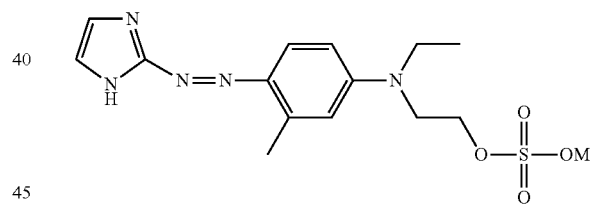

M = H⁺, Na⁺, K⁺

3-{ethyl[4-(1H-imidazol-2-yldiazenyl)-3-methylphenyl]amino}propyl hydrogen sulfate,

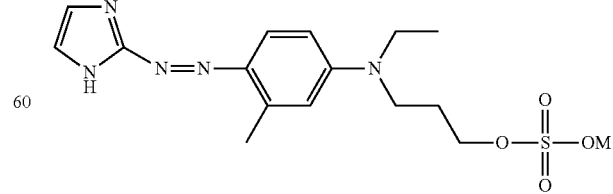

M = H⁺, Na⁺, K⁺

2-{methyl[4-(4H-1,2,4-triazol-3-yldiazenyl)phenyl]amino}ethyl hydrogen sulfate,

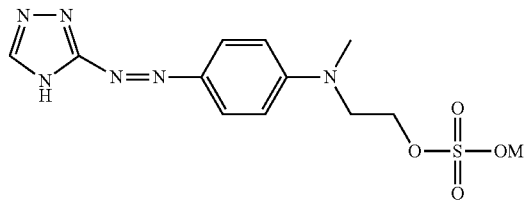

M = H⁺, Na⁺, K⁺

2-{ethyl[4-(4H-1,2,4-triazol-3-yldiazenyl)phenyl]amino}ethyl hydrogen sulfate,

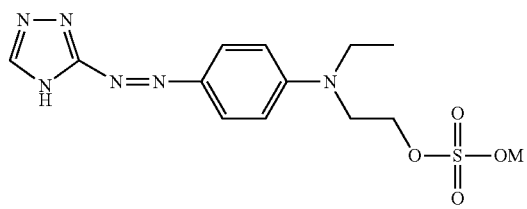

M = H⁺, Na⁺, K⁺

3-{ethyl[4-(4H-1,2,4-triazol-3-yldiazenyl)phenyl]amino}propyl hydrogen sulfate,

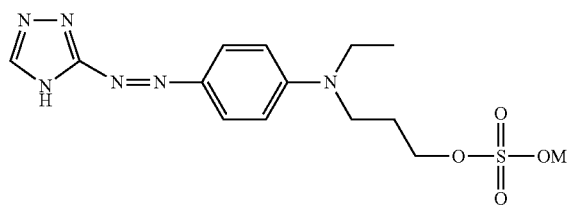

M = H⁺, Na⁺, K⁺

3-{methyl[3-methyl-4-(4H-1,2,4-triazol-3-yldiazenyl)phenyl]amino}propyl hydrogen sulfate,

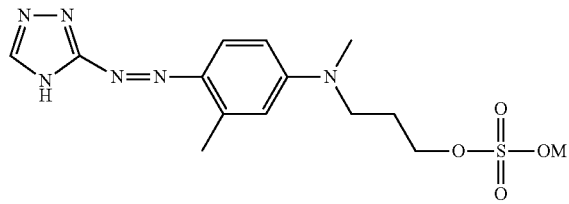

M = H⁺, Na⁺, K⁺

3-{ethyl[3-methyl-4-(4H-1,2,4-triazol-3-yldiazenyl)phenyl]amino}propyl hydrogen sulfate,

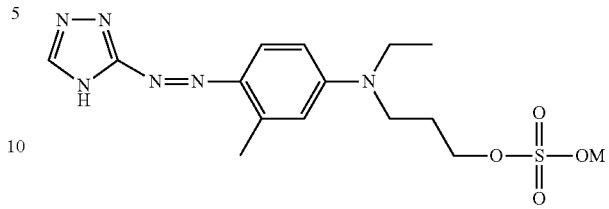

M = H⁺, Na⁺, K⁺

2-{methyl[4-(1,3,4-thiadiazol-2-yldiazenyl)phenyl]amino}ethyl hydrogen sulfate,

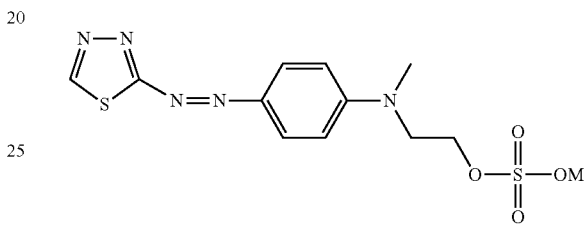

M = H⁺, Na⁺, K⁺

2-{ethyl[4-(1,3,4-thiadiazol-2-yldiazenyl)phenyl]amino}ethyl hydrogen sulfate,

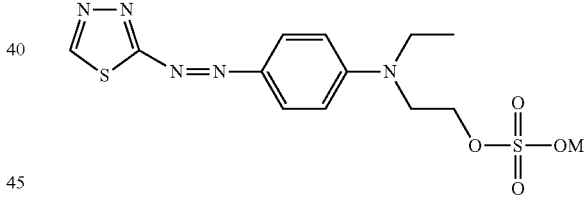

M = H⁺, Na⁺, K⁺

3-{ethyl[4-(1,3,4-thiadiazol-2-yldiazenyl)phenyl]amino}propyl hydrogen sulfate,

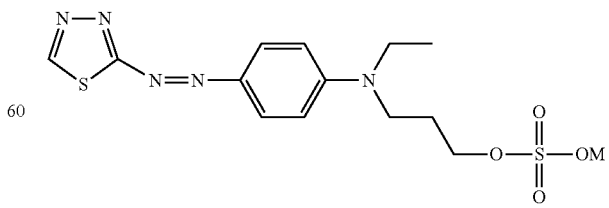

M = H⁺, Na⁺, K⁺

3-{methyl[3-methyl-4-(1,3,4-thiadiazol-2-yldiazenyl)phenyl]amino}propyl hydrogen sulfate,

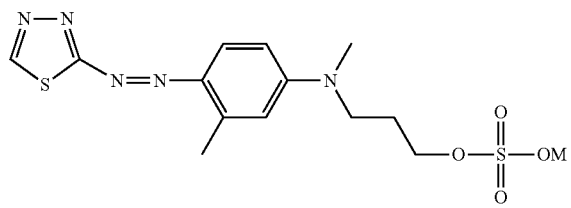

M = H⁺, Na⁺, K⁺

3-{ethyl[3-methyl-4-(1,3,4-thiadiazol-2-yldiazenyl)phenyl]amino}propyl hydrogen sulfate,

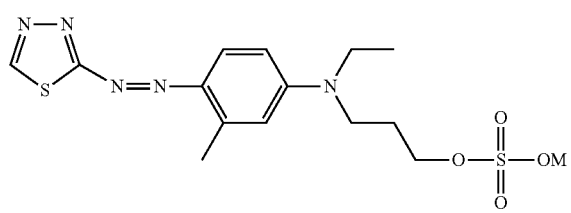

M = H⁺, Na⁺, K⁺

2-{methyl[4-(1,2,4-thiadiazol-5-yldiazenyl)phenyl]amino}ethyl hydrogen sulfate,

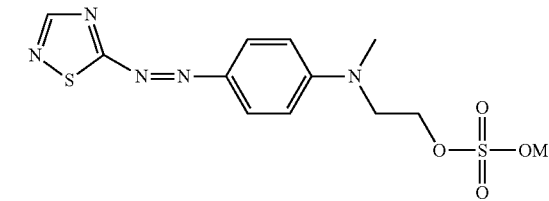

M = H⁺, Na⁺, K⁺

2-{ethyl[4-(1,2,4-thiadiazol-5-yldiazenyl)phenyl]amino}ethyl hydrogen sulfate,

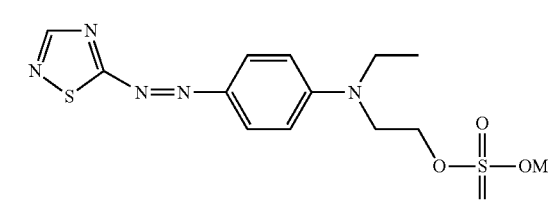

M = H⁺, Na⁺, K⁺

3-{ethyl[4-(1,2,4-thiadiazol-5-yldiazenyl)phenyl]amino}propyl hydrogen sulfate,

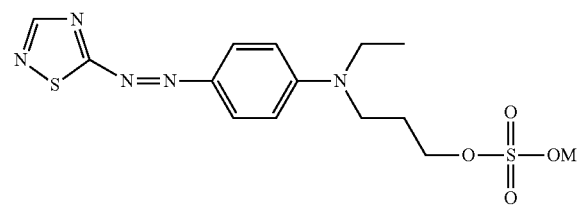

M = H⁺, Na⁺, K⁺

2-{methyl[3-methyl-4-(1,2,4-thiadiazol-5-yldiazenyl)phenyl]amino}ethyl hydrogen sulfate,

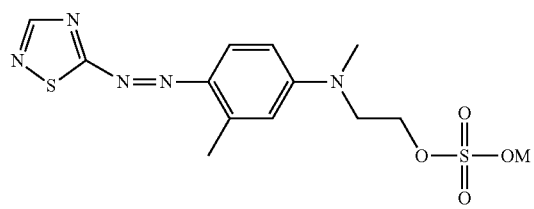

M = H⁺, Na⁺, K⁺

3-{ethyl[3-methyl-4-(1,2,4-thiadiazol-5-yldiazenyl)phenyl]amino}propyl hydrogen sulfate,

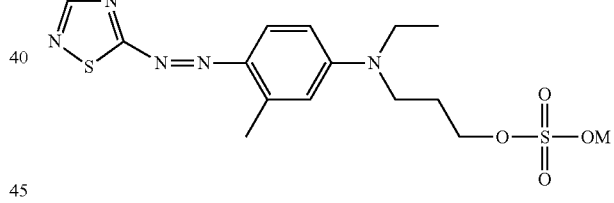

M = H⁺, Na⁺, K⁺

2-{methyl[4-(1,3-benzothiazol-2-yldiazenyl)phenyl]amino}ethyl hydrogen sulfate,

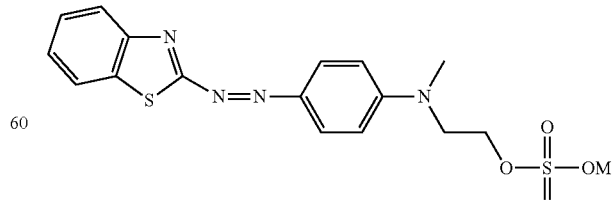

M = H⁺, Na⁺, K⁺

2-{ethyl[4-(1,3-benzothiazol-2-yldiazenyl)phenyl]amino}ethyl hydrogen sulfate,

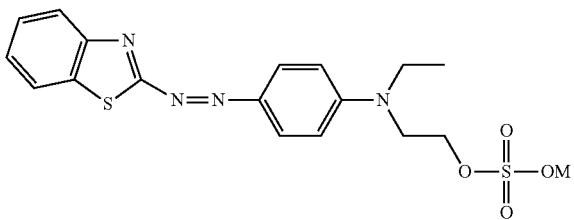

M = H⁺, Na⁺, K⁺

3-{ethyl[4-(1,3-benzothiazol-2-yldiazenyl)phenyl]amino}propyl hydrogen sulfate,

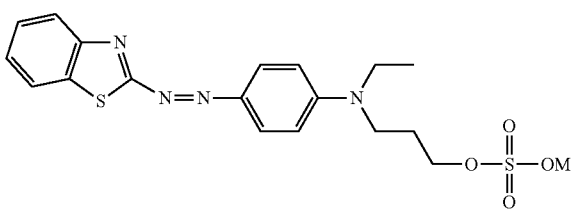

M = H⁺, Na⁺, K⁺

2-{[4-(1,3-benzothiazol-2-yldiazenyl)-3-methylphenyl](methyl)amino}ethyl hydrogen sulfate,

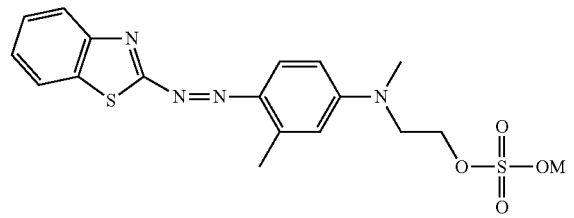

M = H⁺, Na⁺, K⁺

3-{ethyl[4-(1,3-benzothiazol-2-yldiazenyl)-3-methylphenyl]amino}propyl hydrogen sulfate,

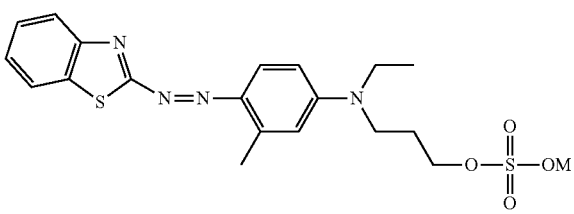

M = H⁺, Na⁺, K⁺

2-{methyl[4-(1,3-benzimidazol-2-yldiazenyl)phenyl]amino}ethyl hydrogen sulfate,

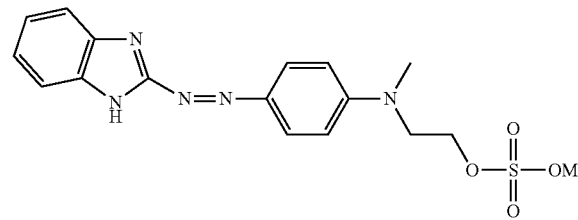

M = H⁺, Na⁺, K⁺

2-{[4-(1,3-benzimidazol-2-yldiazenyl)phenyl](ethyl)amino}ethyl hydrogen sulfate,

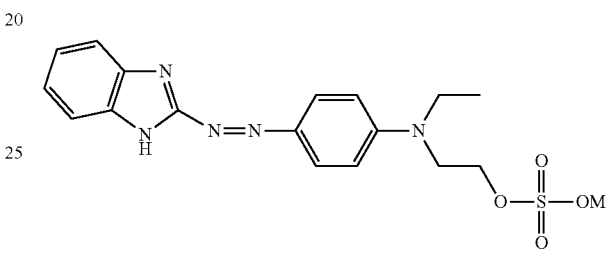

M = H⁺, Na⁺, K⁺

3-{ethyl[4-(1,3-benzimidazol-2-yldiazenyl)phenyl]amino}propyl hydrogen sulfate,

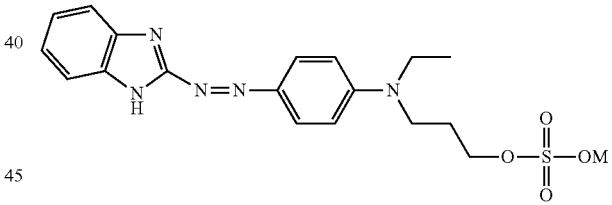

M = H⁺, Na⁺, K⁺

2-{[4-(1,3-benzimidazol-2-yldiazenyl)-3-methylphenyl](methyl)amino}ethyl hydrogen sulfate,

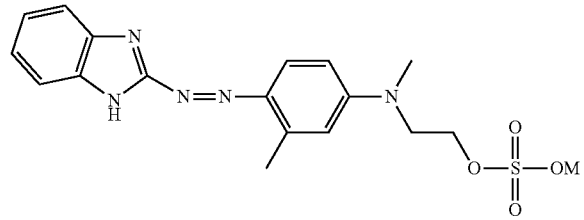

M = H⁺, Na⁺, K⁺

3-{[4-(1,3-benzimidazol-2-yldiazenyl)-3-methylphenyl](ethyl)amino}propyl hydrogen sulfate,

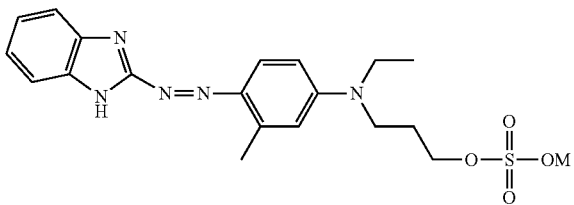

M = H⁺, Na⁺, K⁺

2-[methyl({4-[(E)-2-(1,2-oxazol-5-yl)diazen-1-yl]phenyl})amino]ethyl hydrogen sulfate,

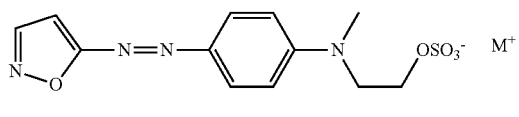

2-[ethyl({4-[(E)-2-(1,2-oxazol-5-yl)diazen-1-yl]phenyl})amino]ethyl hydrogen sulfate,

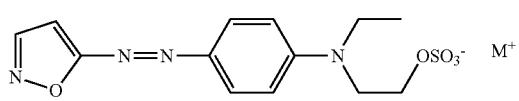

2-[methyl({2-nitro-4-[2-(1,2-oxazol-5-yl)diazen-1-yl]phenyl})amino]ethyl hydrogen sulfate,

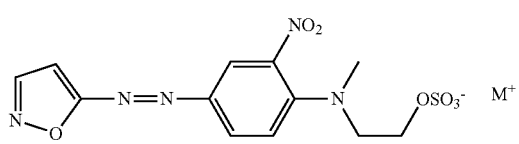

2-[ethyl({2-nitro-4-[2-(1,2-oxazol-5-yl)diazen-1-yl]phenyl})amino]ethyl hydrogen sulfate,

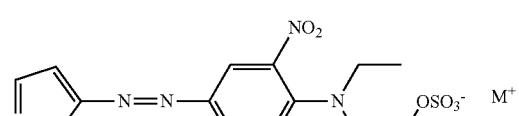

2-[methyl({3-nitro-4-[2-(1,2-oxazol-5-yl)diazen-1-yl]phenyl})amino]ethyl hydrogen sulfate,

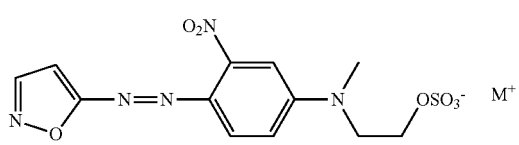

2-[ethyl({3-nitro-4-[2-(1,2-oxazol-5-yl)diazen-1-yl]phenyl})amino]ethyl hydrogen sulfate,

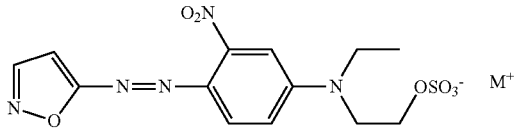

2-[methyl({2-nitro-4-[2-(4H-1,2,4-triazol-3-yl)diazen-1-yl]phenyl})amino]ethyl hydrogen sulfate,

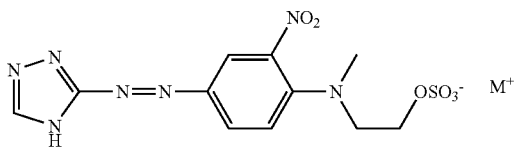

2-[ethyl({2-nitro-4-[2-(4H-1,2,4-triazol-3-yl)diazen-1-yl]phenyl})amino]ethyl hydrogen sulfate,

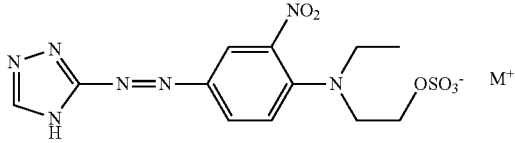

2-[methyl({3-nitro-4-[2-(4H-1,2,4-triazol-3-yl)diazen-1-yl]phenyl})amino]ethyl hydrogen sulfate,

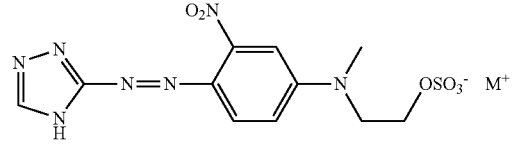

2-[ethyl({3-[2-(4H-1,2,4-triazol-3-yl)diazen-1-yl]phenyl})amino]ethyl hydrogen sulfate,

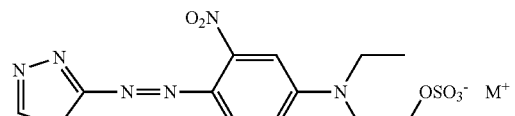

2-[methyl({4-[2-(4-methyl-4H-1,2,4-triazol-3-yl)diazen-1-yl]phenyl})amino]ethyl hydrogen sulfate,

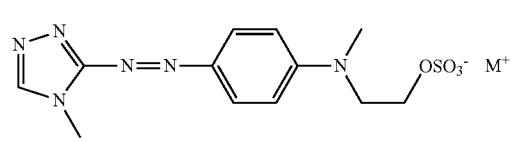

2-[ethyl({4-[2-(4-methyl-4H-1,2,4-triazol-3-yl)diazen-1-yl]phenyl})amino]ethyl hydrogen sulfate,

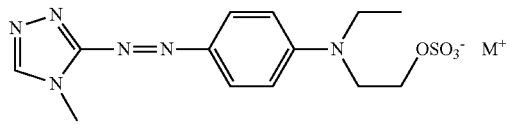

2-[methyl({4-[2-(4-methyl-4H-1,2,4-triazol-3-yl)diazen-1-yl]-2-nitrophenyl})amino]ethyl hydrogen sulfate,

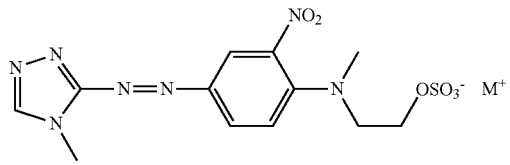

2-[ethyl({4-[2-(4-methyl-4H-1,2,4-triazol-3-yl)diazen-1-yl]-2-nitrophenyl})amino]ethyl hydrogen sulfate,

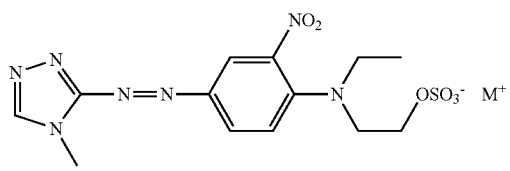

2-[methyl({4-[2-(4-methyl-4H-1,2,4-triazol-3-yl)diazen-1-yl]-3-nitrophenyl})amino]ethyl hydrogen sulfate,

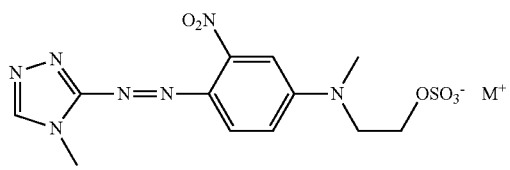

2-[ethyl({4-[2-(4-methyl-4H-1,2,4-triazol-3-yl)diazen-1-yl]-3-nitrophenyl})amino]ethyl hydrogen sulfate,

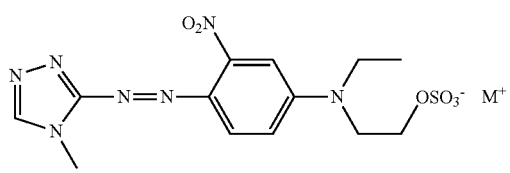

2-[methyl({4-[2-(1-methyl-1H-1,2,4-triazol-3-yl)diazen-1-yl]phenyl})amino]ethyl hydrogen sulfate,

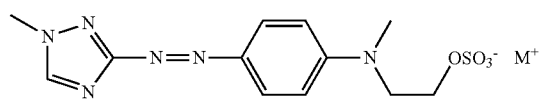

2-[ethyl({4-[2-(1-methyl-1H-1,2,4-triazol-3-yl)diazen-1-yl]phenyl})amino]ethyl hydrogen sulfate,

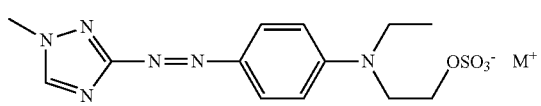

2-[methyl({4-[2-(1-methyl-1H-1,2,4-triazol-3-yl)diazen-1-yl]-2-nitrophenyl})amino]ethyl hydrogen sulfate,

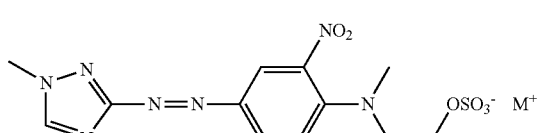

2-[ethyl({4-[2-(1-methyl-1H-1,2,4-triazol-3-yl)diazen-1-yl]-2-nitrophenyl})amino]ethyl hydrogen sulfate,

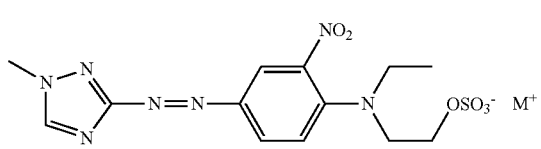

2-[methyl({4-[2-(1-methyl-1H-1,2,4-triazol-3-yl)diazen-1-yl]-3-nitrophenyl})amino]ethyl hydrogen sulfate,

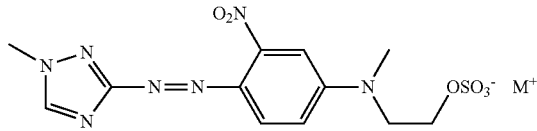

2-[ethyl({4-[2-(1-methyl-1H-1,2,4-triazol-3-yl)diazen-1-yl]-3-nitrophenyl})amino]ethyl hydrogen sulfate,

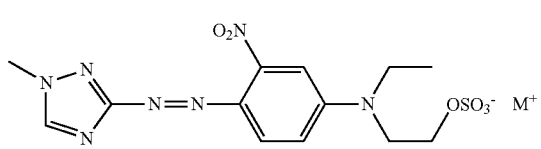

2-[methyl({4-[2-(1,2,4-thiadiazol-5-yl)diazen-1-yl]phenyl})amino]ethyl hydrogen sulfate,

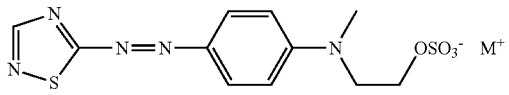

2-[ethyl({4-[2-(1,2,4-thiadiazol-5-yl)diazen-1-yl]phenyl})
amino]ethyl hydrogen sulfate,

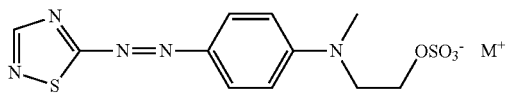

2-[methyl({2-nitro-4-[2-(1,2,4-thiadiazol-5-yl)diazen-1-yl]
phenyl})amino]ethyl hydrogen sulfate,

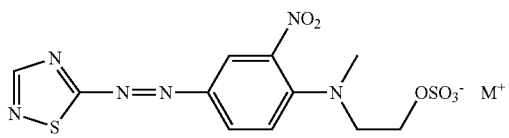

2-[ethyl({2-nitro-4-[2-(1,2,4-thiadiazol-5-yl)diazen-1-yl]
phenyl})amino]ethyl hydrogen sulfate,

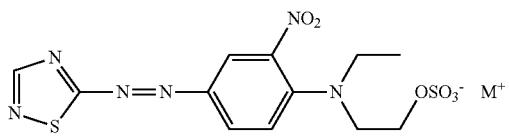

2-[methyl({3-nitro-4-[2-(1,2,4-thiadiazol-5-yl)diazen-1-yl]
phenyl})amino]ethyl hydrogen sulfate,

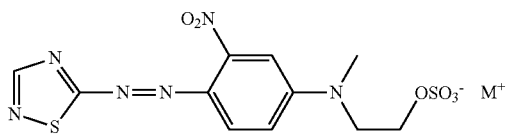

2-[ethyl({3-nitro-4-[2-(1,2,4-thiadiazol-5-yl)diazen-1-yl]
phenyl})amino]ethyl hydrogen sulfate,

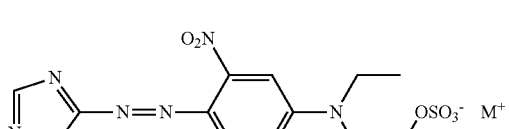

2-[methyl({4-[2-(1,3,4-thiadiazol-2-yl)diazen-1-yl]phenyl})amino]ethyl hydrogen sulfate,

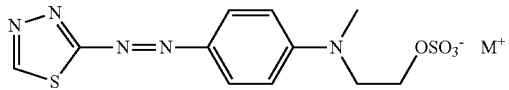

2-[ethyl({4-[2-(1,3,4-thiadiazol-2-yl)diazen-1-yl]phenyl})
amino]ethyl hydrogen sulfate,

2-[methyl({2-nitro-4-[2-(1,3,4-thiadiazol-2-yl)diazen-1-yl]
phenyl})amino]ethyl hydrogen sulfate,

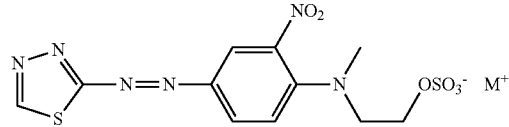

2-[ethyl({2-nitro-4-[2-(1,3,4-thiadiazol-2-yl)diazen-1-yl]
phenyl})amino]ethyl hydrogen sulfate,

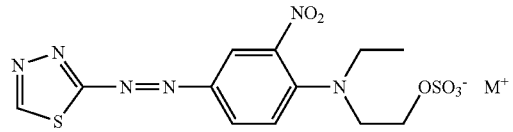

2-[methyl({3-nitro-4-[2-(1,3,4-thiadiazol-2-yl)diazen-1-yl]
phenyl})amino]ethyl hydrogen sulfate,

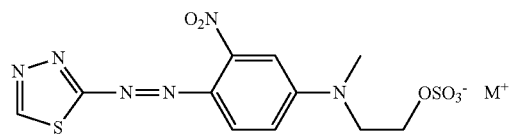

2-[ethyl({3-nitro-4-[2-(1,3,4-thiadiazol-2-yl)diazen-1-yl]
phenyl})amino]ethyl hydrogen sulfate,

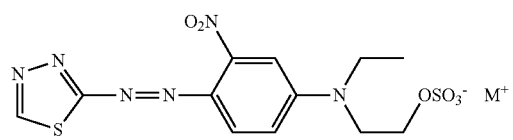

and/or the sodium or potassium salt of one of the above compounds.

In a particularly preferred example, the agent has, as the compound of formula (I), at least one compound selected from 2-{methyl[4-(1,3-thiazol-2-yldiazenyl)phenyl]amino}ethyl hydrogen sulfate, 2-{ethyl[4-(1,3-thiazol-2-yldiazenyl)phenyl]amino}ethyl hydrogen sulfate, 3-{methyl[4-(1,3-thiazol-2-yldiazenyl)phenyl]amino}propyl hydrogen sulfate, 3-{ethyl[4-(1,3-thiazol-2-yldiazenyl)phenyl]amino}propyl hydrogen sulfate, 2-{methyl[4-(4H-1,2,4-triazol-3-yldiazenyl)phenyl]amino}ethyl hydrogen sulfate, 2-{ethyl[4-(4H-1,2,4-triazol-3-yldiazenyl)phenyl]amino}ethyl hydrogen sulfate, 3-{ethyl[4-(4H-1,2,4-triazol-3-yldiazenyl)phenyl]amino}propyl hydrogen sulfate, 2-{methyl[4-(1,2,4-thiadiazol-5-yldiazenyl)phenyl]amino}ethyl hydrogen sulfate, 2-{ethyl[4-(1,2,4-thiadiazol-5-yldiazenyl)phenyl]amino}ethyl hydrogen sulfate, 3-{ethyl[4-(1,2,4- thiadiazol-5-yldiazenyl)phenyl]amino}propyl hydrogen sulfate, 2-{methyl[4-(1,3-benzothiazol-2-yldiazenyl)phenyl]amino}ethyl hydrogen sulfate, 2-{ethyl[4-(1,3-benzothiazol-2-yldiazenyl)phenyl]amino}ethyl hydrogen sulfate, 3-{ethyl[4-(1,3-benzothiazol-2-yldiazenyl)phenyl]amino}propyl hydrogen sulfate, 2-[methyl({4-[(E)-2-(1,2-oxazol-5-yl)diazen-1-yl]phenyl})amino]ethyl hydrogen sulfate, 2-[ethyl({4-[(E)-2-(1,2-oxazol-5-yl)diazen-1-yl]phenyl})amino]ethyl hydrogen sulfate, 2-[ethyl({2-nitro-4-[2-(1,2-oxazol-5-yl)diazen-1-yl]phenyl})amino]ethyl hydrogen sulfate, 2-[ethyl({3-nitro-4-[2-(1,2-oxazol-5-yl)diazen-1-yl]phenyl})amino]ethyl hydrogen sulfate, 2-[ethyl({2-nitro-4-[2-(4H-1,2,4-triazol-3-yl)diazen-1-yl]phenyl})amino]ethyl hydrogen sulfate, 2-[ethyl({3-nitro-4-[2-(4H-1,2,4-triazol-3-yl)diazen-1-yl]phenyl})amino]ethyl hydrogen sulfate, 2-[methyl({4-[2-(4-methyl-4H-1,2,4-triazol-3-yl)diazen-1-yl]phenyl})amino]ethyl hydrogen sulfate, 2-[ethyl({4-[2-(4-methyl-4H-1,2,4-triazol-3-yl)diazen-1-yl]phenyl})amino]ethyl hydrogen sulfate, 2-[ethyl({4-[2-(4-methyl-4H-1,2,4-triazol-3-yl)diazen-1-yl]-2-nitrophenyl})amino]ethyl hydrogen sulfate, 2-[ethyl({4-[2-(4-methyl-4H-1,2,4-triazol-3-yl)diazen-1-yl]-3-nitrophenyl})amino]ethyl hydrogen sulfate, 2-[ethyl({2-nitro-4-[2-(1,2,4-thiadiazol-5-yl)diazen-1-yl]phenyl})amino]ethyl hydrogen sulfate, 2-[ethyl({4-[2-(1-methyl-1H-1,2,4-triazol-3-yl)diazen-1-yl]phenyl})amino]ethyl hydrogen sulfate, 2-[ethyl({4-[2-(1-methyl-1H-1,2,4-triazol-3-yl)diazen-1-yl]2-nitrophenyl})amino]ethyl hydrogen sulfate, 2-[ethyl({3-nitro-4-[2-(1,2,4-thiadiazol-5-yl)diazen-1-yl]phenyl})amino]ethyl hydrogen sulfate, 2-[ethyl({2-nitro-4-[2-(1,3,4-thiadiazol-2-yl)diazen-1-yl]phenyl})amino]ethyl hydrogen sulfate, 2-[ethyl({3-nitro-4-[2-(1,3,4-thiadiazol-2-yl)diazen-1-yl]phenyl})amino]ethyl hydrogen sulfate and/or the sodium or potassium salt of one of the above compounds.

The agents for coloring and optionally simultaneously lightening keratin fibers according to the present specification include the compound(s) of formula (I) preferably in amounts above 1 ppm and below 10 wt. %, relative in each case to the total agent. A preferred example of the agent is characterized in that it includes the compound(s) of formula (I) in a proportion from 0.001 to 5 wt. %, preferably from 0.0025 to 2.5 wt. %, particularly preferably from 0.005 to 2.0 wt. %, and in particular from 0.01 to 1.5 wt. %, relative in each case to the total weight of the agent.

Preferred agents for coloring and optionally simultaneously lightening keratin fibers according to the present specification include at least one compound of formula (I) in a total amount from 0.001 to 5 wt. %, preferably from 0.0025 to 2.5 wt. %, particularly preferably from 0.005 to 2.0 wt. %, and in particular from 0.01 to 1.5 wt. %, relative in each case to the total weight of the agent.

In a further preferred example, the agents include, in addition to the compound of formula (I), at least one further substantive dye. Substantive dyes can be divided into anionic, cationic and non-ionic substantive dyes. The substantive dyes are preferably selected from nitrophenylenediamines, nitroaminophenols, azo dyes, anthraquinones, or indophenols and physiologically acceptable salts thereof. The additional substantive dyes are each preferably used in a proportion from 0.001 to 2 wt. %, relative to the total weight of the agent.

Preferred anionic substantive dyes are the compounds known under the international names or trade names bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic substantive dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 as well as Yellow 87, Basic Orange 31, and Basic Red 51.

Non-ionic nitro and quinone dyes and neutral azo dyes in particular are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

The coloring agents may be used as lightening coloring agents. In order to achieve the lightening effect, the agents may include hydrogen peroxide and/or a solid addition product of hydrogen peroxide with organic or inorganic compounds. Examples of such addition products are addition products of hydrogen peroxide with urea, melamine, and sodium borate.

In order to achieve a stronger lightening and bleaching effect, the agent may include at least one peroxo salt. Suitable peroxo salts are inorganic peroxo compounds, preferably selected from the group formed from ammonium peroxodisulfate, alkali metal peroxodisulfates, ammonium peroxomonosulfate, alkali metal peroxomonosulfates, alkali metal peroxodiphosphates, and alkaline-earth metal peroxides. Peroxodisulfates are particularly preferred, in particular ammonium peroxodisulfate, potassium peroxodisulfate, and sodium peroxodisulfate.

In another example, an agent for coloring and simultaneously lightening keratinic fibers is characterized in that it additionally includes at least one oxidizing agent, selected from sodium persulfate, potassium persulfate, ammonium persulfate, hydrogen peroxide, and one of the solid addition products of hydrogen peroxide with organic or inorganic compounds and mixtures of the above compounds.

In a preferred example, peroxide itself is preferably used as an aqueous solution. The concentration of a hydrogen peroxide solution in the agent according to the present specification is determined on the one hand by legal requirements and on the other by the desired effect; 6 to 12 wt. % solutions in water are preferably used. Ready-to-use agents that are preferred according to the present specification are characterized in that they include 0.5 to 15 wt. %, preferably 1 to 12.5 wt. %, particularly preferably 2.5 to 10 wt. % and in particular 3 to 6 wt. % of hydrogen peroxide, relative in each case to the total weight of the ready-to-use agent.

As used in the present specification and in the appended claims, the term "ready-to-use agent" means the coloring agent in the form in which it is applied to the keratinic fibers. In the case of agents for coloring and simultaneously lightening keratinic fibers, the ready-to-use agent according to the present specification comprises at least one compound of formula (I) and at least one oxidizing agent, selected from sodium persulfate, potassium persulfate, ammonium persulfate, hydrogen peroxide, and/or one of the solid addition products of hydrogen peroxide with organic or inorganic compounds and mixtures of the above compounds.

When the agents additionally include persulfates, these persulfates are preferably included in the agent in an amount from 1.5 to 60 wt. %, preferably 2.0 to 45 wt. %, particularly preferably 2.5 to 40 wt. %, and in particular 5 to 30 wt. %, relative in each case to the total weight of the agent.

To strengthen the bleaching effect, the agent may include further bleaching strength intensifiers, such as for example tetraacetyl ethylene diamine (TAED), 1,5-diacetyl-2,4-dioxohexahydro-1,3,5-triazine (DADHT), tetraacetyl glycoluril (TAGU), N-nonanoyl succinimide (NOSI), n-nonanoyl or isononanoyl oxybenzene sulfonate (n- or i-NOBS), phthalic acid anhydride, triacetin, ethylene glycol diacetate, and 2,5-diacetoxy-2,5-dihydrofuran as well as carbonate salts or hydrogen carbonate salts, in particular ammonium hydrogen carbonate, ammonium carbonate, sodium hydrogen carbonate, disodium carbonate, potassium hydrogen carbonate, dipotassium carbonate, calcium carbonate, and nitrogen-containing, heterocyclic bleaching strength intensifiers, such as 4-acetyl-1-methylpyridinium-p-toluenesulfonate, 2-acetyl-1-methylpyridinium-p-toluenesulfonate as well as N-methyl-3,4-dihydroisoquinolinium-p-toluenesulfonate.

To further increase the lightening, at least one $SiO_2$ compound such as silicic acid or silicates, in particular water glasses, can additionally be added to the composition according to the present specification. It may be preferable, according to the present specification, to use the $SiO_2$ compounds in amounts from 0.05 wt. % to 15 wt. %, particularly preferably in amounts from 0.15 wt. % to 10 wt. %, and most particularly preferably in amounts from 0.2 wt. % to 5 wt. %, relative in each case to the composition according to the present specification. The stated amounts indicate the content of $SiO_2$ compounds, excluding their water component, in the agents.

The agents according to the present specification may be used as oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are selected from at least one compound from the group formed from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, and the physiologically acceptable salts thereof.

Particularly suitable oxidation dye precursors of the coupler type are selected from the group formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds, or the physiologically acceptable salts thereof.

The developer components and coupler components are preferably used in a proportion from 0.0001 to 5.0 wt. %, preferably 0.001 to 2.5 wt. %, relative in each case to the ready-to-use agent. Developer components and coupler components are generally used in approximately equimolar amounts to one another. In some examples, a certain excess of individual oxidation dye precursors is not disadvantageous, such that developer components and coupler components can be in a molar ratio of 1 to 0.5 to 1 to 3, in particular 1 to 1 to 1 to 2.

In the case of oxidation coloring agents, the agents preferably include an oxidizing agent, preferably hydrogen peroxide. The amounts of hydrogen peroxide correspond to the amounts in the lightening agents according to the present specification.

The ready-to-use coloring agents may include additional active ingredients, auxiliary substances and additives to improve the coloring capacity and to establish further desired properties of the agents.

The ready-to-use coloring agents are preferably provided as a liquid preparation and therefore a surface-active substance is additionally added to the agents, such surface-active substances being referred to as surfactants or emulsifiers, depending on the field of application. They are preferably selected from anionic, cationic, zwitterionic, amphoteric and non-ionic surfactants and emulsifiers.

Agents that are preferred according to the present specification are characterized in that the agent additionally includes at least one anionic surfactant. Preferred anionic surfactants are fatty acids, alkyl sulfates, alkyl ether sulfates and ether carboxylic acids with 10 to 20 C atoms in the alkyl group and up to 16 glycol ether groups in the molecule. The anionic surfactants are used in proportions from 0.1 to 45 wt. %, preferably 1 to 30 wt. % and most particularly preferably from 1 to 15 wt. %, relative to the total amount of the ready-to-use agent.

Agents that are preferred according to the present specification are characterized in that the agent additionally includes at least one zwitterionic surfactant. Preferred zwitterionic surfactants are betaines, N-alkyl-N,N-dimethylammonium glycinates, N-acyl aminopropyl-N,N-dimethylammonium glycinates, and 2-alkyl-3-carboxymethyl-3-hydroxyethyl imidazolines. A preferred zwitterionic surfactant is known under the INCI name Cocamidopropyl Betaine.

Agents that are preferred according to the present specification are characterized in that the agent additionally includes at least one amphoteric surfactant. Preferred amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids. Particularly preferred amphoteric surfactants are N-cocoalkyl aminopropionate, cocoacylaminoethyl aminopropionate, and $C_{12}$-$C_{18}$ acyl sarcosine.

It has also proved advantageous for the agents to include further, non-ionogenic interfacially-active substances. Preferred non-ionic surfactants are alkyl polyglycosides as well as alkylene oxide addition products with fatty alcohols and fatty acids, each including 2 to 30 mol of ethylene oxide per mol of fatty alcohol or fatty acid. Preparations having outstanding properties are likewise obtained if they include fatty acid esters of ethoxylated glycerol as non-ionic surfactants.

The non-ionic, zwitterionic or amphoteric surfactants are preferably used in proportions from 0.1 to 45 wt. %, particularly preferably 1 to 30 wt. %, and most particularly preferably from 1 to 15 wt. %, relative to the total amount of the ready-to-use agents.

Agents that are suitable according to the present specification may also include cationic surfactants of the quaternary ammonium compound, esterquat and amidoamine type. Preferred quaternary ammonium compounds are ammonium halides and the imidazolium compounds known under the INCI names Quaternium-27 and Quaternium-83. Further cationic surfactants which may be used according to the present specification are the quaternized protein hydrolysates. A compound from the amido amines that is particularly suitable according to the present specification is the stearamidopropyl dimethylamine which is commercially available under the name Tegoamid® S 18. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. The cationic surfactants are preferably included in the agents used according to the present specification in proportions from 0.05 to 10 wt. %, relative to the total agent.

The ready-to-use coloring agents may include further auxiliary substances and additives. Thus it has proved advantageous if the agents include at least one thickening agent. There are no restrictions in principle regarding these thickening agents. Both organic and also purely inorganic thickening agents can be used.

Suitable thickening agents are anionic, synthetic polymers; cationic, synthetic polymers; naturally occurring thickening agents, such as non-ionic guar gums, scleroglucan gums or xanthan gums, gum arabic, ghatti gum, karaya gum, tragacanth gum, carrageen gum, agar-agar, carob seed meal, pectins, alginates, starch fractions and derivatives such as amylose, amylopectin and dextrins, as well as cellulose derivatives, such as for example methyl cellulose, carboxyalkyl celluloses and hydroxyalkyl celluloses; non-ionic, synthetic polymers, such as polyvinyl alcohol or polyvinyl pyrrolidinone; and inorganic thickening agents, in particular phyllosilicates such as for example bentonite, particularly smectites, such as montmorillonite or hectorite.

Coloring processes on keratin fibers may take place in an alkaline environment. In order to protect the keratin fibers and also the skin as far as possible, it may not be desirable to establish too high a pH, however. It is therefore preferable for the pH of the ready-to-use agent to be between 6 and 11, in particular between 7 and 10.5. The pH values within the meaning of the present specification are pH values measured at a temperature of 22 degrees Celsius (° C.).

The alkalizing agents which may be used according to the present specification to establish the preferred pH may be selected from the group formed from ammonia, alkanol amines, basic amino acids, as well as inorganic alkalizing agents such as alkaline-earth/alkali metal hydroxides, alkaline-earth/alkali metal metasilicates, alkaline-earth/alkali metal phosphates, and alkaline-earth/alkali metal hydrogen phosphates. Preferred inorganic alkalizing agents are magnesium carbonate, sodium hydroxide, potassium hydroxide, sodium silicate, and sodium metasilicate. Organic alkalizing agents that can be used according to the present specification are preferably selected from monoethanolamine, 2-amino-2-methylpropanol, and triethanolamine. The basic amino acids that may be used as the alkalizing agent according to the present specification are preferably selected from the group formed from arginine, lysine, ornithine, and histidine, particularly preferably arginine.

It has furthermore proved advantageous for the coloring agents, in particular if they additionally include hydrogen peroxide, to include at least one stabilizer or complexing agent. Particularly preferred stabilizers are phenacetin, alkali benzoates (sodium benzoate), and salicylic acid. Any complexing agent may be used. Preferred complexing agents according to the present specification are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

The agents according to the present specification may include further active ingredients, auxiliary agents and additives, such as non-ionic polymers (for example vinyl pyrrolidinone/vinyl acrylate copolymers, polyvinyl pyrrolidinone, vinyl pyrrolidinone/vinyl acetate copolymers, polyethylene glycols and polysiloxanes); silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups such as dimethyl-diallyl-ammonium chloride copolymers, dimethylaminoethyl methacrylate-vinyl pyrrolidinone copolymers quaternized with diethyl sulfate, vinyl imidazolinium-methochloride copolymers; zwitterionic and amphoteric polymers; anionic polymers such as for example polyacrylic acids or crosslinked polyacrylic acids; structuring agents such as glucose, maleic acid and lactic acid, hair-conditioning compounds such as phospholipids, for example lecithin and cephalins; perfume oils, dimethyl isosorbide and cyclodextrins; active ingredients to improve the fiber structure, in particular mono-, di- and oligosaccharides such as for example glucose, galactose, fructose, fruit sugars and lactose; dyes for coloring the agent; anti-dandruff active ingredients such as piroctone olamine, zinc omadine and climbazole; amino acids and oligopeptides; protein hydrolysates of animal and/or plant origin as well as those in the form of their fatty acid condensation products or optionally anionically or cationically modified derivatives thereof; vegetable oils; light stabilizers and UV blockers; active ingredients such as panthenol, pantothenic acid, pantolactone, allantoin, pyrrolidinone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, $CO_2$ and air.

These further substances may be selected in accordance with the desired properties of the agents. With regard to further optional components and to the amounts of these components used, reference is expressly made to relevant manuals. The additional active ingredients and auxiliary substances are used in the agents according to the present specification preferably in amounts from 0.0001 to 25 wt. % in each case, in particular 0.0005 to 15 wt. %, relative to the total weight of the application mixture.

A method for coloring keratinic fibers, in particular human hair is described. The method is characterized in that an agent of the present specification is applied to the keratin-containing fibers, left on the fibers for 5 to 60 minutes and then rinsed out again with water or washed out with a shampoo, is suitable in particular for the application of the agents according to the present specification. The contact time of the ready-to-use coloring agents is preferably 5 to 45 minutes, in particular 10 to 40 minutes, particularly preferably 15 to 35 minutes. During the contact time of the agent on the fibers it may be advantageous to support the coloring and/or lightening process by supplying heat. Heat may be supplied both from an external heat source, such as for example hot air from a hot air blower, and also, in particular if the hair coloring and/or hair lightening process is taking place on a living test subject, from the body temperature of the test subject. With the latter option the part to be colored and/or lightened may be covered with a hood. A contact phase at room temperature may also be used according to the present specification. In particular, the temperature during the contact time is between 20° C. and 40° C., in particular between 25° C. and 38° C. After the end of the contact time the remaining coloring preparation is rinsed out of the hair with water or a cleansing agent. A commercial shampoo may be used in particular as the cleansing agent, wherein in particular if the coloring agent and/or lightening agent has a carrier having a high surfactant content the cleansing agent can be dispensed with and the rinsing process can take place with water.

The agents according to the present specification may be formulated as one-component agents (coloring and lightening agent) or as multi-component agents such as two-component agents or three-component agents, and used accordingly. A separation into multi-component systems is useful in particular where incompatibilities between the ingredients are to be expected or feared; in such systems the agent to be used is prepared by the consumer immediately before use by mixing the components together.

A coloring and lightening method in which the lightening cream and the oxidizing agent are initially separate is preferred. The present specification therefore also provides a method for coloring and lightening human hair, wherein a composition on an aqueous basis including hydrogen peroxide is mixed with an agent according to the present specification to form a homogeneous composition (also referred to above as the "ready-to-use agent") and this is applied to the hair.

The compounds of the general formula (I) are very suitable as substantive dyes for hair coloring with a high color intensity and color brilliance. In pigment removal processes, intense and natural color shades are obtained with very good fastness properties. In this way hair can also be simultaneously lightened and colored, allowing a bright color to be achieved even on dark hair.

In coloring agents, the substantive dyes deliver intense shades with no weakening of color intensity and color brilliance when used at the same time as oxidizing agents such as hydrogen peroxide or a mixture of hydrogen peroxide and peroxo disulfates. In this way hair can be simultaneously lightened and colored, allowing even dark hair to be colored.

The present specification further provides the cosmetic use of an agent of the present specification in agents for coloring human hair 1) to improve the color intensity and/or 2) to improve the fastness properties of the color, in particular the wash fastness, light fastness and ultra-bleaching fastness.

All that has been stated in respect of the agents according to the present specification applies with necessary alterations to further preferred examples of the use according to the present specification.

Again, the compounds according to formula (I) are hitherto unknown. The present specification also provides a compound of formula (I), corresponding to the examples of the agent of the present specification.

EXAMPLES

Synthesis Example 1

Synthesis of 2-{ethyl[4-(1,3-thiazol-2-yldiazenyl)phenyl]amino}ethyl sulfate, sodium salt (DZ 1)

1.1. Synthesis of 2-[ethyl(phenyl)amino]ethyl hydrogen sulfate

In 1.1, 16.5 grams (g) (0.10 mol) of 2-(N-ethylanilino)ethanol were added to 25.0 milliliters (ml) of concentrated sulfuric acid at a temperature of 35 to 40 degrees Celsius (° C.). The reaction proceeded slightly exothermically and was held within the specified temperature range by cooling with iced water. The mixture was stirred for an additional 2 hours. On completion of the reaction, the mixture was poured onto ice and made up to 250 ml by adding water. The result was a transparent yellow solution, which was used in the next stage with no further processing.

1.2. Synthesis of 2-{ethyl[4-(1,3-thiazol-2-yldiazenyl)phenyl]amino}ethyl sulfate, sodium salt (DZ 1)

In 1.2, 10.0 g (0.10 mol) of 2-aminothiazole were added to 300 ml of 60 wt. % aqueous acetic acid solution. After adding 20 ml of concentrated sulfuric acid the resulting mixture was cooled to 5° C. Then 40 ml of nitrosyl sulfuric acid (40 wt. %) were added drop-wise and the mixture was stirred for 2 h while cooling to 0° C.

The crude product produced in 1.1 was added, drop-wise, to the previously freshly prepared diazonium salt solution (DZ 1) while cooling to 10° C. The batch was stirred at room temperature overnight. Then a pH of 7 was established by adding a 50% aqueous sodium hydroxide solution. This caused a red solid to be precipitated, which was filtered off and dried. In order to separate the inorganic salts that were still present, the solid was extracted by stirring with ethanol while heating and then filtered. Then the filtrate was completely evaporated again. The yield of the synthesis example 1 is as follows: 31.4 g (88.2%); $^1$H-NMR (400 MHz, DMSO-d$_6$): δ [ppm]=1.17 (s, 3H); 3.56 (q, 2H); 3.70 (t, 2H); 3.94 (t, 2H); 6.92 (d, 2H); 7.68 (d, 1H); 7.79 (d, 2H); 7.92 (d, 1H); $^{13}$C-NMR (400 MHz, DMSO-d$_6$): δ [ppm]=12.4; 45.7; 49.8; 63.5; 112.3; 120.5; 126.9; 141.7; 143.5; 152.5; 178.2.

Synthesis Example 2

Synthesis of 2-{ethyl[4-(4H-1,2,4-triazol-3-yldiazenyl)phenyl]amino}ethyl sulfate, sodium salt (DZ 2)

2.1 Synthesis of 2-[ethyl(phenyl)amino]ethyl hydrogen sulfate. 2.1 is the same as 1.1

2.2. Synthesis of 2-{ethyl[4-(4H-1,2,4-triazol-3-yldiazenyl)phenyl]amino}ethyl sulfate, sodium salt (DZ 2)

In 2.2, 8.4 g (0.10 mol) of 3-amino-1H-1,2,4-triazole were added to 300 ml of 60 wt. % acetic acid solution. After adding 20 ml of concentrated sulfuric acid the resulting mixture was cooled to 5° C. Then 40 ml of nitrosyl sulfuric acid (40 wt. %) were added, drop-wise, and the mixture was stirred for 2 hours while cooling to 0° C.

The crude product of the coupling component produced in 2.1 was added, drop-wise, to the previously freshly prepared diazonium salt solution while cooling to 10° C. The batch was stirred at room temperature overnight. Then a pH of 7 was established by adding a 50% aqueous sodium hydroxide solution. This caused an orange solid to be precipitated, which was filtered off and dried. In order to separate the inorganic salts that were still present, the solid was extracting by stirring with ethanol while heating and then filtered. Then the filtrate was completely evaporated again. The yield of synthesis example 2 is as follows: 8.8 g (26.0%); $^1$H-NMR (400 MHz, DMSO-d$_6$): δ [ppm]=1.15 (s, 3H); 3.44 (q, 2H); 3.69 (t, 2H); 4.20 (t, 2H); 6.71 (d, 2H); 7.60 (d, 2H); 8.29 (s, 1H); $^{13}$C-NMR (400 MHz, DMSO-d$_6$): δ [ppm]=14.7; 48.6; 51.9; 69.0; 114.5; 129.6; 144.8; 148.6; 155.4; 184.0.

Synthesis Example 3

Synthesis of 2-{ethyl[4-(1,3-benzothiazol-2-yldiazenyl)phenyl]amino}ethyl sulfate, sodium salt (DZ 3)

3.1. Synthesis of 2-[ethyl(phenyl)amino]ethyl hydrogen sulfate. 3.1 is the same as 1.1

3.2. Synthesis of 2-{ethyl[4-(4-(1,3-benzothiazol-2-yldiazenyl)phenyl]amino}ethyl sulfate, sodium salt (DZ 3)

In 3.2, 15.0 g (0.10 mol) of 2-aminobenzothiazole were added to 300 ml of 60 wt. % acetic acid solution. After adding 20 ml of concentrated sulfuric acid the resulting mixture was cooled to 5° C. Then 40 ml of nitrosyl sulfuric acid (40 wt. %) were added drop-wise and the mixture was stirred for 2 hours while cooling to 0° C.

Then the crude product of the coupling component produced in 3.1 was added drop-wise to the previously freshly prepared diazonium salt solution (DZ 3) while cooling to 10° C. The batch was stirred at room temperature overnight. Then a pH of 7 was established by adding a 50% aqueous sodium hydroxide solution. This caused an orange solid to be precipitated, which was filtered off and dried. In order to separate the inorganic salts that were still present, the solid was extracting by stirring with ethanol while heating and then filtered. Then the filtrate was completely evaporated again. Yield: 19.8 g (48.9%).

Pigment Removal Examples 1.1 Production of the coloring creams. A number of coloring creams were produced.

1.1.1.—A non-ionic coloring cream as defined in Table (1) was produced.

TABLE (1)

| | |
|---|---|
| Cetearyl alcohol | 6.0 g |
| Coconut alcohol | 6.0 g |
| PEG-40 hydrogenated castor oil | 1.0 g |
| Ceteareth-12 | 3.0 g |
| Ceteareth-20 | 3.0 g |
| Methylparaben | 0.3 g |
| Propylparaben | 0.2 g |
| Phenoxyethanol | 1.0 g |
| PEG-8 | 5.0 g |
| DZ according to the present specification | 1.0 g |
| Ammonium sulfate | 1.0 g (in 30.0 g water) |
| Hydroxyethylcellulose | 1.0 g (in 15.0 g water) |
| NaOH 0.1% | to pH |
| Water | to 100 g |

The first nine components of Table (1) were melted together at 80° C., then the dye, pre-dissolved in a small amount of water, was added. This mixture was emulsified with a solution of ammonium sulfate in 30 g of water. Then a swelling solution of 1.0 g of hydroxyethylcellulose in 15.0 g of water was added. The pH indicated in Table 1 was established with a 0.1% sodium hydroxide solution, then the mixture was made up to 100 g with water.

1.1.2—A cationic coloring cream as defined in Table (2) was produced.

TABLE (2)

| | |
|---|---|
| Cetearyl alcohol | 4.0 g |
| Ceteareth-12 | 1.0 g |
| Dehyquart ® A-CA | 2.0 g |
| Ammonium sulfate | 1.0 g (in 30.0 g water) |
| DZ according to the present specification | 1.0 g |
| Water | to 100 g |

Referencing Table (2), Cetearyl alcohol was melted together with Ceteareth-12 and Dehyquart® A-CA, then the melt was emulsified with hot water. Then the dye, pre-dissolved in a little water, and the aqueous ammonium sulfate solution were added. The pH was adjusted to the value indicated in the Table (2) with ammonia or citric acid, then the mixture was made up to 100 g with water.

1.1.3—An anionic coloring cream as defined in Table (3) was produced.

TABLE (3)

| | |
|---|---|
| Cetearyl alcohol | 1.0 g |
| Coconut alcohol | 1.0 g |
| Akypo Soft ® RLM 45N | 1.1 g |
| Propylparaben | 0.1 g |
| Methylparaben | 0.1 g |
| Ammonium sulfate | 1.0 g (in 30.0 g water) |
| DZ according to the present specification | 1.0 g |
| Water | to 100 g |

The first five components of Table (3) were melted together. This melt was emulsified with hot water, then the dye, pre-dissolved in water, was added along with the ammonium sulfate solution. The pH indicated in the Table (3) was established with ammonia or citric acid, then the mixture was made up to 100 g with water.

1.2—Below is a more detailed list of the raw materials indicated in Tables (1)-(3). Akypo RLM 45 NV® refers to lauryl alcohol-4.5-EO acetic acid sodium salt with a minimum 22% active substance content (INCI name: Sodium Laureth-5 Carboxylate). Dehyquart® A-CA refers to trimethyl hexadecyl ammonium chloride with approximately 24-26% active substance (INCI name: Aqua (Water), Cetrimonium Chloride).

1.3 Pigment removal—In the pigment removal process, 1.8 g of each coloring cream (as defined by Tables (1)-(3)) was applied to an approximately 6 cm long strand of human hair (Kerling Euronaturhaar, blond) and left there for 30 min at 30° C. At the end of the contact time the hair was rinsed, washed with a hair washing agent and then dried. The hair strands were colored in the shades indicated in Table (4). In Table (4), DZ 1 refers to 2-{Ethyl[4-(1,3-thiazol-2-yldiazenyl)phenyl]amino}ethyl sulfate, sodium salt; DZ 2 refers to 2-{Ethyl[4-(4H-1,2,4-triazol-3-yldiazenyl)phenyl]amino}ethyl sulfate, sodium salt; and DZ 3 refers to 2-{Ethyl[4-(1,3-benzothiazol-2-yldiazenyl)phenyl]amino}ethyl sulfate, sodium salt.

TABLE (4)

| Dye | Coloring cream | pH | Shade | Intensity |
|---|---|---|---|---|
| DZ 1 | 1 | 7.0 | nasturtium red | +++ |
| DZ 1 | 1 | 9.5 | garnet red | +++ |
| DZ 1 | 2 | 7.0 | garnet red | +++ |
| DZ 1 | 2 | 9.5 | pigment red | +++ |
| DZ 1 | 3 | 7.0 | coral red | +++ |
| DZ 1 | 3 | 9.5 | pigment red | +++ |
| DZ 2 | 1 | 7.0 | orange | +++ |
| DZ 2 | 1 | 9.5 | red orange | +++ |
| DZ 2 | 2 | 7.0 | apricot yellow | +++ |
| DZ 2 | 2 | 9.5 | orange | +++ |
| DZ 2 | 3 | 7.0 | yellow orange | +++ |
| DZ 2 | 3 | 9.5 | orange | +++ |
| DZ 3 | 1 | 7.0 | matt red | ++ |
| DZ 3 | 1 | 9.5 | garnet red | ++ |
| DZ 3 | 2 | 7.0 | gray red | ++ |
| DZ 3 | 2 | 9.5 | red | ++ |
| DZ 3 | 3 | 7.0 | gray red | ++ |
| DZ 3 | 3 | 9.5 | port red | ++ |

In Table (4), a "+" in the Intensity column indicates low intensity, "++" indicates medium intensity, and "+++" indicates high intensity.

1.4 Wash fastness—Next, washing fastness was tested. In this test, the pigment was removed from hair strands (Kerling, Euronaturhaar, white) using the anionic coloring cream obtained in 1.1.3 (indicated in Table (3)), pH 9.5, including DZ 1, and the strands were dried and measured by colorimetry (Spectralflash SF 450, Datacolor). To determine the wash fastness, the strands were washed by hand six times. To this end, the strands were first dampened with water and then shampooed for 45 seconds in each case with a 25% Texapon NSO-UP solution. The shampooed hair was rinsed thoroughly for 1 minute with hand-hot water. Then the hair strand was dried with a hair dryer. The next washing process took place after drying. After six hair washes the strands were measured again by colorimetry.

Table (5) indicates the color characteristics of hair treated with DZ 1 after 0 hair washes and after 6 washes as measured in the Lab color space.

TABLE (5)

| | Kerling (Euronaturhaar, white) | | |
|---|---|---|---|
| DZ 1 | L | a | b |
| 0 hair washes | 39.15 | 43.59 | 25.98 |
| 6 hair washes | 44.95 | 44.78 | 25.32 |

Both a visual comparison of the unwashed and washed hair strand and a comparison of the colorimetric data, as indicated in Table (5) reveal that the compound according to the present specification exhibits excellent wash fastness.

1.5 Light Fastness—Next, the light fastness, according to DIN 54004, was tested. In this test, the hair strands dyed with the anionic coloring cream of Table (3) obtained using the pigment removal process described in 1.3 were exposed to light for 120 hours in a Xenotest device (Hanau). At the same time, fabric light fastness scales (with light fastness values from 1 to 6) were exposed to light as a reference. At the end of the exposure time, the light fastness (LF) of the compound according to the present specification was assessed by visual comparison with the fabric light fastness scales. The light fastness of a substantive dye was rated as good if the light fastness value was 3 or more. Table (6) presents the light fastness scale for the coloring cream of Table (3).

TABLE (6)

| Coloring cream 3, DZ1 | LF = 4. |
|---|---|

In Table (6), an LF value of 1 corresponds to very poor light fastness and an LF value of 6 corresponds to a very good light fastness.

1.6 Ultra-bleaching fastness—Next, the ultra-bleaching fastness was tested. In this test, a bleaching cream as defined by Table (7) was produced.

TABLE (7)

| Description | wt. % |
|---|---|
| Cetearyl alcohol | 11.00 |
| Coconut alcohol | 2.75 |
| Ceteareth-20 | 0.25 |
| Sodium laureth sulfate, 27 wt. % | 26.50 |
| Ammonium sulfate | 1.00 |
| Etidronic acid, 60 wt. % | 0.20 |
| Sodium silicate | 0.50 |
| Wheat protein hydrolysate, 40 wt. % | 0.35 |
| DZ 1: 2-{Ethyl[4-(1,3-thiazol-2-yldiazenyl)phenyl]amino}ethyl sulfate, sodium salt | 2.00 |
| Vitamin F | 1.00 |
| Ammonia, 25 wt. % | 7.60 |
| Perfume | qs |
| Water | to 100 |

The bleaching cream of Table (7) was mixed in the ratio 1:1 with an oxidizing agent dispersion as defined in Table (8):

TABLE (8)

| Description | wt. % |
|---|---|
| Sodium hydroxide, 45 wt. % | 0.73 |
| Dipicolinic acid | 0.10 |
| Dis odium pyrophosphate | 0.03 |

TABLE (8)-continued

| Description | wt. % |
|---|---|
| Etidronic acid, 60 wt. % | 1.50 |
| Sodium laureth sulfate, 27 wt. % | 2.00 |
| Dimethicone, 10 wt. % | 0.07 |
| Acrylates copolymer, approx. 30 wt. % | 12.00 |
| Hydrogen peroxide, 50 wt. % | 22.40 |
| Water | to 100 |

Then 0.37 parts of ammonium persulfate were added to this mixture (ammonium persulfate content of 27.0 wt. % in the application mixture). After homogenizing the mixture, a ready-to-use booster bleaching agent was obtained, 1.8 g of which was applied in each case to an approximately 6 centimeter (cm) long strand of human hair (Kerling Euronaturhaar, blond) and left there for 30 min at 30° C. At the end of the contact time the hair was rinsed, washed with a hair washing agent and then dried. The DZ 1 color (2-{Ethyl[4-(1,3-thiazol-2-yldiazenyl)phenyl]amino}ethyl sulfate, sodium salt) was obtained. Table (9) indicates the characteristics of the obtained color.

TABLE (9)

| Dye | Coloring cream | pH | Shade | Intensity |
|---|---|---|---|---|
| DZ 1 | 3 | 9.5 | pigment red | +++ |

In Table (9), a "+" in the Intensity column indicates low intensity, "++" indicates medium intensity, and "+++" indicates high intensity.

The coloring result obtained in this way was visually compared with the coloring results obtained in 1.3—the pigment removal process. The comparison showed that when pigment was removed in the presence of a mixture of hydrogen peroxide and persulfates, a brilliant color was obtained which showed no weakening of the color intensity in comparison to the formulation without an oxidizing agent.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for coloring keratinic fibers, the agent comprising, in a cosmetic carrier, at least one compound of formula (I),

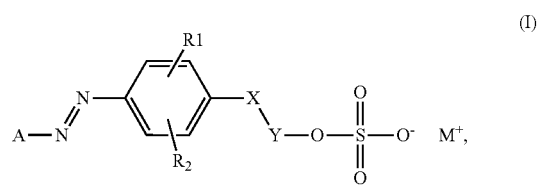

in which:

R1 and R2:
  independently of one another denote hydrogen, a $C_1$-$C_6$ alkyl group, a $C_2$-$C_6$ alkenyl group, a hydroxyl group, a halogen, a $C_1$-$C_6$ alkoxy group, an amino group, a nitro group, an acetyl amino group, or a sulfonamide group; or when in ortho-position to one another, form a 5- or 6-membered, saturated or unsaturated ring, which optionally comprise further heteroatoms;

X denotes O or N—R3;

R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a cyano-$C_1$-$C_6$ alkyl group, or a —Y'—O—$SO_2$—$O^-$ $M^+$ group;

Y and Y' independently of one another denote $(CH_2)_n$, $C_2H_4$—$(OC_2H_4)_n$, $(CH_2)_n$—O—$(CH_2)_m$, or $(CH_2)_n$—N(R6')-$(CH_2)_m$, in which n, and optionally m, each denote a whole number from 1 to 6;

A denotes one of the structures (II) to (XV),

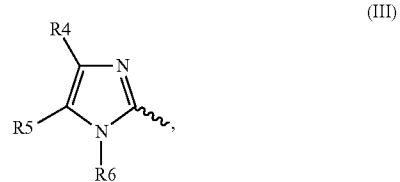

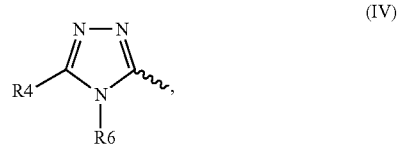

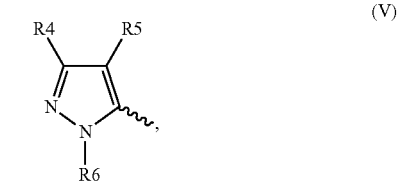

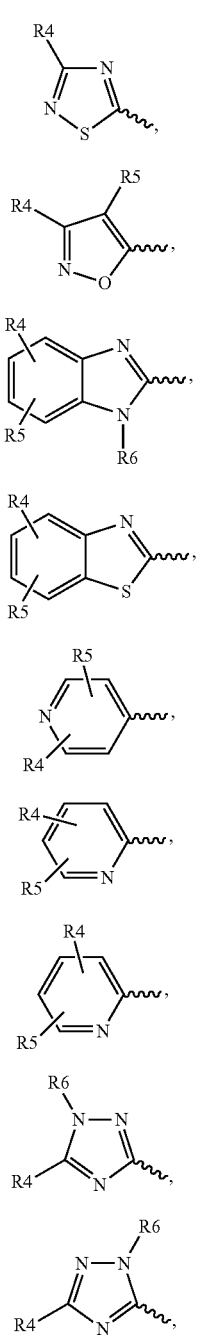

R4 and R5
   independently of one another denote hydrogen, an amino group, a $C_1$-$C_6$ alkylamino group, a di-($C_1$-$C_6$ alkyl)amino group, a hydroxyl group, a $C_1$-$C_6$ alkoxy group, a $C_1$-$C_6$ alkyl group, a $C_2$-$C_6$ alkenyl group, a carboxylic acid group, a sulfonic acid group, a halogen, an acetylamino group, or a sulfonamide group; or
   when in ortho-position to one another, form a 5- or 6-membered, saturated or unsaturated ring, which optionally includes further heteroatoms;

R6 and R6' each independently of one another denote a hydrogen atom, a $C_1$-$C_6$ alkyl group, a $C_2$-$C_6$ alkenyl group, or a $C_2$-$C_6$ hydroxyalkyl group; and $M^+$ denotes a proton ($H^+$), an alkali metal cation, or a half equivalent of an alkaline-earth metal cation.

2. The agent of claim 1, in which A denotes one of the structures (II), (III), (IV), (VI), (VII), (X), or (XIV).

3. The agent of claim 1, in which:
   X denotes N—R3; and
   Y denotes $(CH_2)_n$, where n equals 2 or 3.

4. The agent of claim 1, in which:
   X denotes N—R3; and
   R3 denotes a $C_1$-$C_6$ alkyl group.

5. The agent of claim 1, in which R1 and R2 independently of one another denote hydrogen, a $C_1$-$C_6$ alkyl group, or a nitro group.

6. The agent of claim 1, in which R1 and R2 each denote hydrogen.

7. The agent of claim 1, in which:
   R1 denotes hydrogen; and
   R2 denotes a nitro group.

8. The agent of claim 1, in which the at least one compound of formula (I) is selected from the group consisting of: 2-{methyl[4-(1,3-thiazol-2-yldiazenyl)phenyl]amino}ethyl hydrogen sulfate, 2-{ethyl[4-(1,3-thiazol-2-yldiazenyl)phenyl]amino}ethyl hydrogen sulfate, 3-{methyl[4-(1,3-thiazol-2-yldiazenyl)phenyl]amino}propyl hydrogen sulfate, 3-{ethyl[4-(1,3-thiazol-2-yldiazenyl)phenyl]amino}propyl hydrogen sulfate, 2-{methyl[3-methyl-4-(1,3-thiazol-2-yldiazenyl)phenyl]amino}ethyl hydrogen sulfate, 3-{ethyl[3-methyl-4-(1,3-thiazol-2-yldiazenyl)phenyl]amino}propyl hydrogen sulfate, 2-{[4-(1H-imidazol-2-yldiazenyl)phenyl](methyl)amino}ethyl hydrogen sulfate, 2-{ethyl[4-(1H-imidazol-2-yldiazenyl)phenyl]amino}ethyl hydrogen sulfate, 3-{ethyl[4-(1H-imidazol-2-yldiazenyl)phenyl]amino}propyl hydrogen sulfate, 2-{ethyl[4-(1H-imidazol-2-yldiazenyl)-3-methylphenyl]amino}ethyl hydrogen sulfate, 3-{ethyl[4-(1H-imidazol-2-yldiazenyl)-3-methylphenyl]amino}propyl hydrogen sulfate, 2-{methyl[4-(4H-1,2,4-triazol-3-yldiazenyl)phenyl]amino}ethyl hydrogen sulfate, 2-{ethyl[4-(4H-1,2,4-triazol-3-yldiazenyl)phenyl]amino}ethyl hydrogen sulfate, 3-{ethyl[4-(4H-1,2,4-triazol-3-yldiazenyl)phenyl]amino}propyl hydrogen sulfate, 3-{methyl[3-methyl-4-(4H-1,2,4-triazol-3-yldiazenyl)phenyl]amino}propyl hydrogen sulfate, 3-{ethyl[3-methyl-4-(4H-1,2,4-triazol-3-yldiazenyl)phenyl]amino}propyl hydrogen sulfate, 2-{methyl[4-(1,3,4-thiadiazol-2-yldiazenyl)phenyl]amino}ethyl hydrogen sulfate, 2-{ethyl[4-(1,3,4-thiadiazol-2-yldiazenyl)phenyl]amino}ethyl hydrogen sulfate, 3-{ethyl[4-(1,3,4-thiadiazol-2-yldiazenyl)phenyl]amino}propyl hydrogen sulfate, 3-{methyl[3-methyl-4-(1,3,4-thiadiazol-2-yldiazenyl)phenyl]amino}propyl hydrogen sulfate, 3-{ethyl[3-methyl-4-(1,3,4-thiadiazol-2-yldiazenyl)phenyl]amino}propyl hydrogen sulfate, 2-{methyl[4-(1,2,4-thiadiazol-5-yldiazenyl)phenyl]amino}ethyl hydrogen sulfate, 2-{ethyl[4-(1,2,4-thiadiazol-5-yldiazenyl)phenyl]amino}ethyl hydrogen sulfate, 3-{ethyl[4-(1,2,4-thiadiazol-5-yldiazenyl)phenyl]amino}propyl hydrogen sulfate, 2-{methyl[3-methyl-4-(1,2,4-thiadiazol-5-yldiazenyl)phenyl]amino}ethyl hydrogen sulfate, 3-{ethyl[3-methyl-4-(1,2,4-thiadiazol-5-yldiazenyl)phenyl]amino}propyl hydrogen sulfate, 2-{methyl[4-(1,3-benzothiazol-2-yldiazenyl)phenyl]amino}ethyl hydrogen sulfate, 2-{ethyl[4-(1,3-benzothiazol-2-yldiazenyl)phenyl]amino}ethyl hydrogen sulfate, 3-{ethyl[4-(1,3-benzothiazol-2-yldiazenyl)phenyl]amino}propyl hydrogen sulfate, 2-{[4-(1,3-benzothiazol-2-yldiazenyl)-3-methylphenyl](methyl)amino}ethyl hydrogen sulfate, 3-{ethyl[4-(1,3-benzothiazol-2-yldiazenyl)-3-methylphenyl]amino}propyl hydrogen sulfate, 2-{methyl[4-(1,3-benzimidazol-2-yldiazenyl)phenyl]amino}ethyl hydrogen sulfate, 2-{[4-(1,3-benzimidazol- 2-yldiazenyl)phenyl](ethyl)amino}ethyl hydrogen sulfate, 3-{ethyl[4-(1,3-benzimidazol-2-yldiazenyl)phenyl]amino}propyl hydrogen sulfate, 2-{[4-(1,3-benzimidazol-2-yldiazenyl)-3-methylphenyl](methyl)amino}ethyl hydrogen sulfate, 3-{[4-(1,3-benzimidazol-2-yldiazenyl)-3-methylphenyl](ethyl)amino}propyl hydrogen sulfate, 2-[methyl({4-[(E)-2-(1,2-oxazol-5-yl)diazen-1-yl]phenyl})amino]ethyl hydrogen sulfate, 2-[ethyl({4-[(E)-2-(1,2-oxazol-5-yl)diazen-1-yl]phenyl})amino]ethyl sulfate, 2-[methyl({2-nitro-4-[2-(1,2-oxazol-5-yl)diazen-1-yl]phenyl})amino]ethyl hydrogen sulfate, 2-[ethyl({2-nitro-4-[2-(1,2-oxazol-5-yl)diazen-1-yl]phenyl})amino]ethyl hydrogen sulfate, 2-[methyl({3-nitro-4-[2-(1,2-oxazol-5-yl)diazen-1-yl]phenyl})amino]ethyl hydrogen sulfate, 2-[ethyl({3-nitro-4-[2-(1,2-oxazol-5-yl)diazen-1-yl]phenyl})amino]ethyl hydrogen sulfate, 2-[methyl({4-[2-(4H-1,2,4-triazol-3-yl)diazen-1-yl]phenyl})amino]ethyl hydrogen sulfate, 2-[ethyl({4-[2-(4H-1,2,4-triazol-3-yl)diazen-1-yl]phenyl})amino]ethyl hydrogen sulfate, 2-[methyl({2-nitro-4-[2-(4H-1,2,4-triazol-3-yl)diazen-1-yl]phenyl})amino]ethyl hydrogen sulfate, 2-[ethyl({2-nitro-4-[2-(4H-1,2,4-triazol-3-yl)diazen-1-yl]phenyl})amino]ethyl hydrogen sulfate, 2-[methyl({3-nitro-4-[2-(4H-1,2,4-triazol-3-yl)diazen-1-yl]phenyl})amino]ethyl hydrogen sulfate, 2-[ethyl({3-[2-(4H-1,2,4-triazol-3-yl)diazen-1-yl]phenyl})amino]ethyl hydrogen sulfate, 2-[methyl({4-[2-(4-methyl-4H-1,2,4-triazol-3-yl)diazen-1-yl]phenyl})amino]ethyl hydrogen sulfate, 2-[ethyl({4-[2-(4-methyl-4H-1,2,4-triazol-3-yl)diazen-1-yl]phenyl})amino]ethyl hydrogen sulfate, 2-[methyl({4-[2-(4-methyl-4H-1,2,4-triazol-3-yl)diazen-1-yl]-2-nitrophenyl})amino]ethyl hydrogen sulfate, 2-[ethyl({4-[2-(4-methyl-4H-1,2,4-triazol-3-yl)diazen-1-yl]-2-nitrophenyl})amino]ethyl hydrogen sulfate, 2-[methyl({4-[2-(4-methyl-4H-1,2,4-triazol-3-yl)diazen-1-yl]-3-nitrophenyl})amino]ethyl hydrogen sulfate, 2-[ethyl({4-[2-(4-methyl-4H-1,2,4-triazol-3-yl)diazen-1-yl]-3-nitrophenyl})amino]ethyl hydrogen sulfate, 2-[methyl({4-[2-(1-methyl-1H-1,2,4-triazol-3-yl)diazen-1-yl]phenyl})amino]ethyl hydrogen sulfate, 2-[ethyl({4-[2-(1-methyl-1H-1,2,4-triazol-3-yl)diazen-1-yl]phenyl})amino]ethyl hydrogen sulfate, 2-[methyl({4-[2-(1-methyl-1H-1,2,4-triazol-3-yl)diazen-1-yl]-2-nitrophenyl})amino]ethyl hydrogen sulfate, 2-[ethyl({4-[2-(1-methyl-1H-1,2,4-triazol-3-yl)diazen-1-yl]-2-nitrophenyl})amino]ethyl hydrogen sulfate, 2-[methyl({4-[2-(1-methyl-1H-1,2,4-triazol-3-yl)diazen-1-yl]-3-nitrophenyl})amino]ethyl hydrogen sulfate, 2-[ethyl({4-[2-(1-methyl-1H-1,2,4-triazol-3-yl)diazen-1-yl]-3-nitrophenyl})amino]ethyl hydrogen sulfate, 2-[methyl({4-[2-(1,2,4-thiadiazol-5-yl)diazen-1-yl]phenyl})amino]ethyl hydrogen sulfate, 2-[ethyl({4-[2-(1,2,4-thiadiazol-5-yl)diazen-1-yl]phenyl})amino]ethyl hydrogen sulfate, 2-[methyl({2-nitro-4-[2-(1,2,4-thiadiazol-5-yl)diazen-1-yl]phenyl})amino]ethyl hydrogen sulfate, 2-[ethyl({2-nitro-4-[2-(1,2,4-thiadiazol-5-yl)diazen-1-yl]phenyl})amino]ethyl hydrogen sulfate, 2-[methyl({3-nitro-4-[2-(1,2,4-thiadiazol-5-yl)diazen-1-yl]phenyl})amino]ethyl hydrogen sulfate, 2-[ethyl({3-nitro-4-[2-(1,2,4-thiadiazol-5-yl)diazen-1-yl]phenyl})amino]ethyl hydrogen sulfate, 2-[methyl({4-[2-(1,3,4-thiadiazol-2-yl)diazen-1-yl]phenyl})amino]ethyl hydrogen sulfate, 2-[ethyl({4-[2-(1,3,4-thiadiazol-2-yl)diazen-1-yl]phenyl})amino]ethyl hydrogen sulfate, 2-[methyl({2-nitro-4-[2-(1,3,4-thiadiazol-2-yl)diazen-1-yl]phenyl})amino]ethyl hydrogen sulfate, 2-[ethyl({2-nitro-4-[2-(1,3,4-thiadiazol-2-yl)diazen-1-yl]phenyl})amino]ethyl hydrogen sulfate, 2-[methyl({3-nitro-4-[2-(1,3,4-thiadiazol-2-yl)diazen-1-yl]phenyl})amino]ethyl hydrogen sulfate, 2-[ethyl({3-nitro-4-[2-(1,3,4-thiadiazol-2-yl)diazen-1-yl]phenyl})amino]ethyl hydrogen sulfate, and the sodium or potassium salt of one of the above compounds.

9. The agent of claim 1, characterized in that the at least one compound of formula (I) forms between 0.001 to 5 wt. % of a total weight of the agent.

10. The agent of claim 1, further comprising at least one oxidizing agent, selected from the group consisting of sodium persulfate, potassium persulfate, ammonium persulfate, hydrogen peroxide, and one of the solid addition products of hydrogen peroxide with organic or inorganic compounds and mixtures of the above compounds.

11. The agent of claim 1, further comprising at least one oxidation dye precursor.

12. The agent of claim 1, further comprising at least one surface-active substance selected from anionic, cationic, zwitterionic, amphoteric and non-ionic surfactants and emulsifiers.

13. The agent of claim 1, characterized in that the pH of the agent, measured at a temperature of 22 degrees Celcius, is between 6 and 11.

14. The agent of claim 1, in which the agent is used to improve the color intensity of hair, to improve the fastness properties of hair color, or combinations thereof.

15. A compound of formula (I),

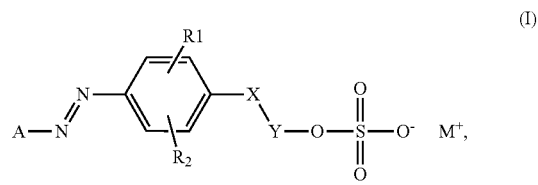

in which:
R1 and R2:
  independently of one another denote hydrogen, a $C_1$-$C_6$ alkyl group, a $C_2$-$C_6$ alkenyl group, a hydroxyl group, a halogen, a $C_1$-$C_6$ alkoxy group, an amino group, a nitro group, an acetyl amino group, or a sulfonamide group; or
  when in ortho-position to one another, form a 5- or 6-membered, saturated or unsaturated ring, which optionally comprise further heteroatoms;
X denotes O or N—R3;
R3 denotes hydrogen, a $C_1$-$C_6$ alkyl group, a $C_2$-$C_6$ alkenyl group, a $C_2$-$C_6$ hydroxyalkyl group, a $C_2$-$C_6$ polyhydroxyalkyl group, a cyano-$C_1$-$C_6$ alkyl group, or a —Y'—O—$SO_2$—$O^-$ $M^+$ group;
Y and Y' independently of one another denote $(CH_2)_n$, $C_2H_4$—$(OC_2H_4)_n$, $(CH_2)_n$—O—$(CH_2)_m$, or $(CH_2)_n$—N(R6')-$(CH_2)_m$, in which n, and optionally m, each denote a whole number from 1 to 6;
A denotes one of the structures (II) to (XV),

-continued

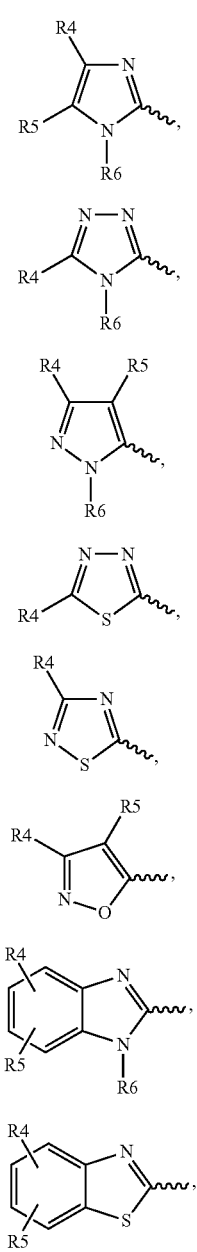

(III)
(IV)
(V)
(VI)
(VII)
(VIII)
(IX)
(X)

-continued

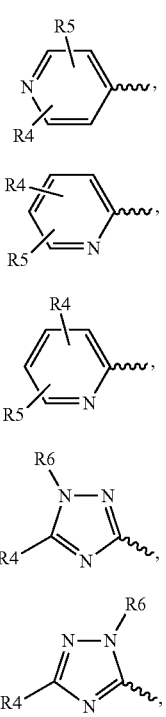

(XI)
(XII)
(XIII)
(XIV)
(XV)

R4 and R5
  independently of one another denote hydrogen, an amino group, a $C_1$-$C_6$ alkylamino group, a di-($C_1$-$C_6$ alkyl)amino group, a hydroxyl group, a $C_1$-$C_6$ alkoxy group, a $C_1$-$C_6$ alkyl group, a $C_2$-$C_6$ alkenyl group, a carboxylic acid group, a sulfonic acid group, a halogen, an acetylamino group, or a sulfonamide group; or
  when in ortho-position to one another, form a 5- or 6-membered, saturated or unsaturated ring, which optionally includes further heteroatoms;

R6 and R6' each independently of one another denote a hydrogen atom, a $C_1$-$C_6$ alkyl group, a $C_2$-$C_6$ alkenyl group, or a $C_2$-$C_6$ hydroxyalkyl group; and $M^+$ denotes a proton ($H^+$), an alkali metal cation, or a half equivalent of an alkaline-earth metal cation.

\* \* \* \* \*